(12) United States Patent
Cutillas et al.

(10) Patent No.: US 12,360,118 B2
(45) Date of Patent: Jul. 15, 2025

(54) METHOD FOR PROTEIN KINASE ACTIVITY RANKING

(71) Applicant: KINOMICA LIMITED, Macclesfield (GB)

(72) Inventors: Pedro Rodriguez Cutillas, London (GB); Edmund Wilkes, London (GB); Pedro Casado-Izquierdo, London (GB)

(73) Assignee: KINOMICA LIMITED, Macclesfield (GB)

( * ) Notice: Subject to any disclaimer, the term of this patent is extended or adjusted under 35 U.S.C. 154(b) by 2041 days.

(21) Appl. No.: 15/776,161

(22) PCT Filed: Nov. 16, 2016

(86) PCT No.: PCT/EP2016/077845
§ 371 (c)(1),
(2) Date: May 15, 2018

(87) PCT Pub. No.: WO2017/085116
PCT Pub. Date: May 26, 2017

(65) Prior Publication Data
US 2020/0249239 A1    Aug. 6, 2020
US 2021/0223258 A9    Jul. 22, 2021

(30) Foreign Application Priority Data

Nov. 16, 2015 (GB) .................................. 1520178

(51) Int. Cl.
*G01N 33/68*    (2006.01)
*G16B 20/20*    (2019.01)
*G16B 40/10*    (2019.01)
*G16H 20/00*    (2018.01)

(52) U.S. Cl.
CPC ......... *G01N 33/6848* (2013.01); *G16B 20/20* (2019.02); *G16B 40/10* (2019.02); *G16H 20/00* (2018.01); *G01N 2440/00* (2013.01); *G01N 2800/52* (2013.01)

(58) Field of Classification Search
None
See application file for complete search history.

(56) References Cited

U.S. PATENT DOCUMENTS

| | | |
|---|---|---|
| 6,818,484 B2 | 11/2004 | Voutsas |
| 2003/0153007 A1 | 8/2003 | Chen et al. |
| 2005/0164324 A1 | 7/2005 | Gygi |
| 2006/0148093 A1 | 7/2006 | Gygi et al. |
| 2008/0221802 A1 | 9/2008 | Oda et al. |
| 2012/0070844 A1* | 3/2012 | Rodriguez Cutillas ..... G01N 33/6848 435/7.1 |

FOREIGN PATENT DOCUMENTS

| | | |
|---|---|---|
| EP | 2124051 | 11/2009 |
| EP | 2013054764 | 12/2013 |
| WO | 2003097867 | 11/2003 |
| WO | 2003102220 | 12/2003 |
| WO | 2005106923 | 11/2005 |
| WO | 2007127767 | 11/2007 |
| WO | 2007144606 | 12/2007 |
| WO | 2009054939 | 4/2009 |
| WO | 2010006333 | 1/2010 |
| WO | 2010040024 | 4/2010 |
| WO | 2010119261 | 10/2010 |
| WO | 2011109440 | 9/2011 |
| WO | 2013132075 | 12/2013 |

OTHER PUBLICATIONS

H Patterson, R Nibbs, I McInnes, S Siebert, Protein kinase inhibitors in the treatment of inflammatory and autoimmune diseases, Clinical and Experimental Immunology, vol. 176, Issue 1, Apr. 2014, pp. 1-10 (Year: 2014).*
Liebler DC, Zimmerman LJ. Targeted quantitation of proteins by mass spectrometry. Biochemistry. Jun. 4, 2013;52(22):3797-806. (Year: 2013).*
McLachlin DT, Chait BT. Analysis of phosphorylated proteins and peptides by mass spectrometry. Curr Opin Chem Biol. Oct. 2001;5(5):591-602. (Year: 2001).*
Wu HY, Tseng VS, Liao PC. Mining phosphopeptide signals in liquid chromatography-mass spectrometry data for protein phosphorylation analysis. J Proteome Res. May 2007;6(5):1812-21. (Year: 2007).*
Schumacher JA, Crockett DK, Elenitoba-Johnson KS, Lim MS. Evaluation of enrichment techniques for mass spectrometry: identification of tyrosine phosphoproteins in cancer cells. J Mol Diagn. Apr. 2007;9(2):169-77. (Year: 2007).*
Di Palma S, Hennrich ML, Heck AJ, Mohammed S. Recent advances in peptide separation by multidimensional liquid chromatography for proteome analysis. J Proteomics. Jul. 16, 2012;75(13):3791-813. (Year: 2012).*

(Continued)

*Primary Examiner* — Olivia M. Wise
*Assistant Examiner* — Jonathan Edward Hayes
(74) *Attorney, Agent, or Firm* — Perkins Coie LLP; Viola Kung; Andrew T. Pettit

(57) ABSTRACT

The present invention provides a method of quantifying the activity of a protein modifying enzyme in a sample, comprising calculating the value K for said protein-modifying enzyme on the basis of the number of modified peptides in a sample that are substrates of said protein modifying enzyme, the intensity of the modified peptides, each modified peptide in the sample that is a substrate of said protein modifying enzyme, the total number of modified peptides in the sample, the intensity of the modified peptides and all of the modified peptides in the sample. A method of quantifying the activity of a protein modifying enzyme in a sample, comprising calculating the value SC for said protein-modifying enzyme on the basis of a reduction in proliferation using an inhibitor at an inhibitor concentration at which proliferation is measured and the "in vitro" IC50i of the inhibitor against a primary target is also provided. The invention further provides methods of identifying inhibitors with which to treat a patient, methods of treatment, a computer readable medium, a computer program product and devices for carrying out the methods.

17 Claims, 14 Drawing Sheets

(56) References Cited

OTHER PUBLICATIONS

Figure 1:
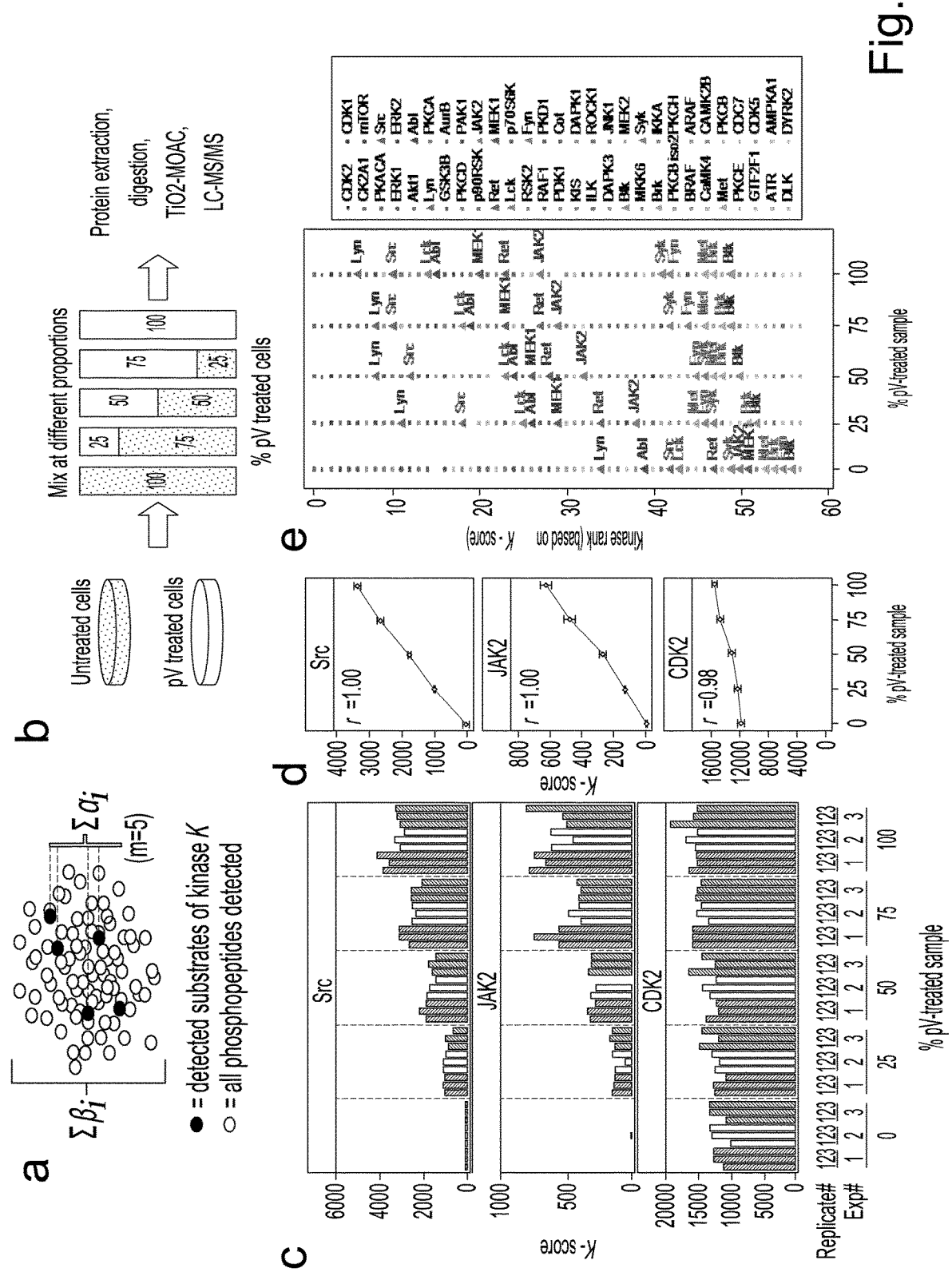

Worthington, J., Cutillas, P.R. and Timms, J.F. (2011), IMAC/TiO2 enrich for peptide modifications other than phosphorylation: Implications for chromatographic choice and database searching in phosphoproteomics. Proteomics, 11: 4583-4587. (Year: 2011).*
Alcolea MP, Cutillas PR. In-depth analysis of protein phosphorylation by multidimensional ion exchange chromatography and mass spectrometry. Methods Mol Biol. 2010;658:111-26. (Year: 2010).*
Salovska, Barbora, Tichy, Ales, Rezacova, Martina, Vavrova, Jirina and Novotna, Eva. "Enrichment strategies for phosphoproteomics: state-of-the-art" Reviews in Analytical Chemistry, vol. 31, No. 1, 2012, pp. 29-41. (Year: 2012).*
Engholm-Keller K, Birck P, Størling J, Pociot F, Mandrup-Poulsen T, Larsen MR. TiSH—a robust and sensitive global phosphoproteomics strategy employing a combination of TiO2, SIMAC, and HILIC. J Proteomics. Oct. 22, 2012;75(18):5749-61. (Year: 2012).*
Roskoski R Jr. A historical overview of protein kinases and their targeted small molecule inhibitors. Pharmacol Res. Oct. 2015;100:1-23. (Year: 2015).*
Wilkes "Phosphoproteomic investigation of kinase signalling network plasticity in response to chronic PI3K and mTORC1/2 inhibition" Thesis submitted on Feb. 5, 2015 and made available Sep. 30, 2015.
Vojvodic et al., "A Phosphoproteomics approach to identify candidate kinase inhibitor pathway targets in lymphoma-like primary cell lines", Current Drug Discovery Technologies, 2013, 10, pp. 283-304.
Rix et al., "Chemical proteomic profiles of the BCR-ABL inhibitors imatinib, nilotinib and dasatinib reveal novel kinase and nonkinase targets", Blood, 2007, 110(12), pp. 4055-4063.
Pan et al., "Global Effects of kinase inhibitors on signalling networks revealed by quantitative phosphoproteomics", Molecular and Cellular Proteomics, 2009, 8.12, pp. 2796-2808.
Wilkes et al., "Deep analysis of signaling plasticity in a breast cancer kinase network during acquisition of resistance to PI3K and mTORC1/2 inhibitors", NCRI Cancer Conference abstract, 2013.
Wilkes et al., "Empirical inference of circuitry and plasticity in a kinase signalling network" PNAS, 2015, 112(25), pp. 7719-7724.
Kholodenko et al., "Untangling the wires: A strategy to trace functional interactions in signaling and gene networks", PNAS, 2002, 99(20), pp. 12841-12846.
Mukherjee et al., "Network inference using informative priors", PNAS, 2008, 105(38), pp. 14313-14318.
Prill et al., "Crowdsourcing Network Inference: The DREAM Predictive Signaling Network Challenge", Sci Signal, 2012, 4(189), mr7.
Linding et al., "Systematic Discovery of In Vivo Phosphorylation Networks", Cell, 2007, 129(7), pp. 1415-1426.
Carlson et al., "Large-scale Discovery of ERK2 Substrates Identifies ERK-Mediated Transcriptional Regulation by ETV3", Sci Signal. 2013, 4(196): rs11.
Bensimon et al., "Mass Spectrometry-Based Proteomics and Network Biology", Annu Rev Biochem, 2012, 81, pp. 379-405.
Casado et al., "Kinase-substrate enrichment analysis provides insights into the heterogeneity of signalling pathway activation in leukaemia cells", Science Signalling, 2013, 6(268):rs6.
Casado et al., "Phosphoproteomics data classify hematological cancer cell lines according to tumor type and sensitivity to kinase inhibitors", Genome Biology, 2013, 14:R37.
Bolstad et al., "A Comparison of Normalization Methods for High Density Oligonucleotide Array Data Based on Variance and Bias", Bioinformatics, 2003, 19(2), pp. 185-193.
Smyth, "Linear Models and Empirical Bayes Methods for Assessing Differential Expression in Microarray Experiments", Stat Appl Genet Molec Biol, 2004, 3(1), Article 3.
R Core Team (2013), http://www.R-project.org, 2013.
Alcolea et al., "Phosphoproteomic Analysis of Leukemia Cells under Basal and Drug-treated Conditions Identifies Markers of Kinase Pathway Activation and Mechanisms of Resistance", Mol Cell Proteomics, 2012, 11.8, pp. 453-466.

Tsou et al.,"IDEAL-Q, an automated tool for label-free quantitation analysis using an efficient peptide alignment approach and spectral data validation", Mol Cell Proteomics, 2009, 9.1, pp. 131-144.
Mann et al., "ProteinQuant Suite: a bundle of automated software tools for label-free quantitative proteomics", Rapid Commun Mass Spectrom, 2008, 22, pp. 3823-3834.
Escher et al., "Using iRT, a normalized retention time for more targeted measurement of peptides", Proteomics, 2012, 12, pp. 1111-1121.
Wickham, "Elegant Graphics for Data Analysis", Journal of Statistical Software, 2010, 35(1), pp. 1-3.
Warnes et al., "Various R programming tools for plotting data", Package 'gplots', 2016, 3.0.1, pp. 1-68.
Wickham, "Reshaping data with the reshape package", http://had.co.nz/reshape, 2006, pp. 1-25.
Csardi et al., "The igraph software package for complex network research", InterJournal Complex Systems:1695, 2005, pp. 1-9.
Shannon et al., "RCytoscape: tools for exploratory network analysis", BMC Bioinformatics, 2013, 14(217), pp. 1-9.
Shannon et al., "Cytoscape: a software environment for integrated models of biomolecular interaction networks", Genome Res, 2003, 13(11), pp. 2498-2504.
Gobbi et al., "Fast randomization of large genomic datasets while preserving alteration counts", Bioinformatics, 2014, 30, pp. i617-i623.
Kim et al., "PAGE: parametric analysis of gene set enrichment", BMC Bioinformatics, 2005, 6(144), pp. 1-12.
Lindsley et al., "Allosteric Akt (PKB) inhibitors: discovery and SAR of isozyme selective inhibitors", Bioorg Med Chem Lett, 2005, 15, pp. 761-764.
Rehan et al., "Computational insights into the inhibitory mechanism of human AKT1 by an orally active inhibitor, MK-2206", PLoS One, 2014, 9(10):e109705.
Hirai et al., "MK-2206, an allosteric Akt inhibitor, enhances the antitumor efficacy by standard chemotherapeutic agents or molecular targeted drugs in vitro and in vivo", Mol Cancer Ther, 2010, 9(7), pp. 1956-1967.
Sumi et al., "The newly synthesized selective Ca2+/calmodulin dependent protein kinase-II inhibitor KN-93 reduces dopamine contents in PC12H cells", Biochem Biophys Res Commun, 1991, 181(3), pp. 968-975.
Tokumitsu et al., "KN-62, 1-N,O-bis(5-isoquinolinesulfonyl)-N-methyl-L-tyrosyl 4-phenylpiperazin E, a specific inhibitor of Ca2+/calmodulin-dependent protein kinase-II", J Biol Chem, 1990, 265(8), pp. 4315-4320.
Fry et al., "Specific, irreversible inactivation of the epidermal growth factor receptor and erbB2, by a new class of tyrosine kinase inhibitor", PNAS, 1998, 95, pp. 12022-12027.
Bos et al., "PD153035, a tyrosine kinase inhibitor, prevents epidermal growth factor receptor activation and inhibits growth of cancer cells in a receptor number-dependent manner", Clin Cancer Res, 1997, 3, pp. 2099-2106.
Hancock et al., "Identification of novel extracellular signal-regulated kinase docking domain inhibitors", J Med Chem, 2005, 48, pp. 4586-4595.
Ohori et al., "Identification of a selective ERK inhibitor and structural determination of the inhibitor-ERK2 complex", Biochem Biophys Res Commun, 2005, 336, pp. 357-363.
Gilmartin et al., "GSK1120212 (JTP-74057) Is an Inhibitor of MEK Activity and Activation with Favorable Pharmacokinetic Properties for Sustained In Vivo Pathway Inhibition", Clin Cancer Res, 2011, 17(5), pp. 989-1000.
Roberts et al., "Targeting the Raf-MEK-ERK mitogen-activated protein kinase cascade for the treatment of cancer", Oncogene, 2007, 26, pp. 3291-3310.
Favata et al., "Identification of a novel inhibitor of mitogen-activated protein kinase kinase", J Biol Chem, 1998, 273(29), pp. 18623-18632.
Garcia-Martinez et al., "Ku-0063794 is a specific inhibitor of the mammalian target of rapamycin (mTOR)", Biochem J, 2009, 421, pp. 29-42.
Liu et al., "Discovery of 1-(4-(4-Propionylpiperazin-1-yl)-3-(trifluoromethyl)phenyl)-9-(quinolin- 3-yl)benzo h 1,6 naphthyridin-

(56) References Cited

OTHER PUBLICATIONS

2(1H) one as a Highly Potent, Selective Mammalian Target of Rapamycin (mTOR) Inhibitor for the Treatment of Cancer", J Med Chem, 2010, 53(19), pp. 7146-7155.
Pearce et al., "Characterization of PF-4708671, a novel and highly specific inhibitor of p70 ribosomal S6 kinase (S6K1)", Biochem J, 2010, 431, pp. 245-255.
Okuzumi et al., "Inhibitor hijacking of Akt activation", Nat Chem Biol, 2009, 5(7), pp. 484-493.
Raynaud et al., "Biological properties of potent inhibitors of class I phosphatidylinositide 3-kinases: from PI-103 through PI-540, PI-620 to the oral agent GDC-0941", Mol Cancer Ther, 2010, 8(7), pp. 1725-1738.
Martiny-Baron et al., "Selective inhibition of protein kinase C isozymes by the indolocarbazole Gö 6976", J Biol Chem, 1993, 268(13), pp. 9194-9197.
Toullec et al., "The bisindolylmaleimide GF-109203X is a potent and selective inhibitor of protein kinase C", J Biol Chem, 1991, 266(24), pp. 15771-15781.
McCluskey et al., "Serine-threonine protein phosphatase inhibitors: Development of potential therapeutic strategies", J Med Chem, 2002, 45(6), pp. 1151-1175.
Li et al., "Cantharidin-binding protein—identification as protein phosphatase-2A", PNAS, 1992, 89, pp. 11867-11870.
Tamura et al., "Development of specific Rho-kinase inhibitors and their clinical application", Biochim Biophys Acta, 2005, 1754, pp. 245-252.
Shizaki et al., "Pharmacological properties of Y-27632, a specific inhibitor of Rho-associated kinases", Mol Pharmacol, 2000, 57, pp. 976-983.
Du et al., "Cancer systems biology: embracing complexity to develop better anticancer therapeutic strategies", Oncogene, 2015, 34, pp. 3215-3225.
Papin et al., "Reconstruction of cellular signaling networks and analysis of their properties", Nat Rev Mol Cell Biol, 2005, 6, pp. 99-111.
Jorgensen et al., "Simplistic pathways or complex networks?", Curr Opin Genet Dev, 2010, 20, pp. 15-22.
Hsu et al., "The mTOR-regulated phosphoproteome reveals a mechanism of mTORC1-mediated inhibition of growth factor signaling", Science, 2011, 332(6035), pp. 1317-1322.
Goltsov et al., "Features of the reversible sensitivity-resistance transition in PI3K/PTEN/AKT signaling network after HER2 inhibition", Cell Signal, 2012, 24, pp. 493-504.
Goltsov et al., "Compensatory effects in the PI3K/PTEN/AKT signaling network following receptor tyrosine kinase inhibition", Cell Signal, 2011, 23, pp. 407-416.
Posch et al., "Combined targeting of MEK and PI3K/mTOR effector pathways is necessary to effectively inhibit NRAS mutant melanoma in vitro and in vivo", PNAS, 2013, 110(10), pp. 4015-4020.
Renshaw et al., "Dual blockade of the PI3K/AKT/mTOR (AZD8055) and RAS/MEK/ERK (AZD6244) pathways synergistically inhibits rhabdomyosarcoma cell growth in vitro and in vivo", Clin Cancer Res, 2013, 19(21), pp. 5940-5951.
Roberts et al., "Combined PI3K/mTOR and MEK inhibition provides broad antitumor activity in faithful murine cancel models", Clin Cancer Res, 2012, 18(19), pp. 5290-5303.
Sarbassov et al., "Rictor, a novel binding partner of mTOR, defines a rapamycin-insensitive and raptor-independent pathway that regulates the cytoskeleton", Curr Biol, 2004, 14, pp. 1296-1302.
Hay et al., "Upstream and downstream of mTOR", Genes Dev, 2004, 18, pp. 1926-1945.
Kumar et al., "Activation of a non-genomic Pim-1/Bad-Pser75 module is required for an efficient pro-survival effect of Bcl-xL induced by androgen in LNCaP cells", Int J Biochem Cell Biol, 2011, 43, pp. 594-603.
Vincent et al., "Control of cell survival by IGF signaling pathways", Growth Horm IGF Res, 2002, 12, pp. 193-197.

Ciaccio et al., "Systems analysis of EGF receptor signaling dynamics with microwestern arrays", Nat Methods, 2010, 7(2), pp. 148-155.
Munugalavadla et al., "The PI3K inhibitor GDC-0941 combines with existing clinical regimens for superior activity in multiple myeloma", Oncogene, 2014, 33, pp. 316-325.
Oda et al., "A comprehensive pathway map of epidermal growth factor receptor signaling", Mol Sys Biol, 2005, 2005.0010.
Kanehisa et al., "KEGG for integration and interpretation of large-scale molecular data sets", Nucleic Acids Res, 2012, 40, Database issue:D109-114.
Dutta et al., "A network-based, integrative study to identify core biological pathways that drive breast cancer clinical subtypes", Br J Cancer, 2012, 106, pp. 1107-1116.
Hughes et al., "Functional discovery via a compendium of expression profiles", Cell, 2000, 102, pp. 109-126.
Muranen et al., "Inhibition of PI3K/mTOR leads to adaptive resistance in matrix-attached cancer cells", Cancer Cell, 2012, 21(2), pp. 227-239.
Elkabets et al., "mTORC1 Inhibition Is Required for Sensitivity to PI3K p110 alpha Inhibitors in PIK3CA-Mutant Breast Cancer", Sci Transl Med, 2013, 5(196): 196ra99.
Klempner et al., "What a Tangled Web We Weave: Emerging Resistance Mechanisms to Inhibition of the Phosphoinositide 3-Kinase Pathway", Cancer Discov, 2013, 3(12), pp. 1345-1354.
Lito et al., "Tumor adaptation and resistance to RAF inhibitors", Nat Med, 2013, 19(11), pp. 1401-1409.
Gerlinger et al., "Intratumor heterogeneity and branched evolution revealed by multiregion sequencing", N Eng J Med, 2012, 366(10), pp. 883-892.
Le Gac et al., "Ecological and evolutionary dynamics of coexisting lineages during a long-term experiment with *Escherichia coli*", PNAS, 2012, 109(24), pp. 9487-9492.
Samovski et al., "Regulation of AMPK activation by CD36 links fatty acid uptake to beta-oxidation", Diabetes, 2015, 64, pp. 353-359.
Liu et al., "Activated STING in a vascular and pulmonary syndrome", The New England journal of medicine, 2014, 371(6), pp. 507-518.
Forlenza et al., "Increased platelet GSK3B activity in patients with mild cognitive impairment and Alzheimer's disease", Journal of psychiatric research, 2011, 45, pp. 220-224.
Samuels et al., "Oncogenic mutations of PIK3CA in human cancers", Cell cycle, 2004, 3(10), pp. e17-e19.
Manning, "Challenges and opportunities in defining the essential cancer kinome", Sci Signal, 2009, 2(63), pe15.
Schlabach et al., "Cancer proliferation gene discovery through functional genomics", Science, 2008, 319(5863), pp. 620-624.
Grueneberg et al., "Kinase requirements in human cells: I. Comparing kinase requirements across various cell types", PNAS, 2008, 105(43), pp. 16472-16477.
Grueneberg et al., "Kinase requirements in human cells: IV. Differential kinase requirements in cervical and renal human tumor cell lines", PNAS, 2008, 105(43), pp. 16490-16495.
Chapman et al., "Improved survival with vemurafenib in melanoma with BRAF V600E mutation", The New England Journal of Medicine, 2011, 364(26), pp. 2507-2516.
Janku et al., "PI3K/AKT/mTOR inhibitors in patients with breast and gynecologic malignancies harboring PIK3CA mutations", Journal of Clinical Oncology, 2012, 30(8), pp. 777-782.
Casado et al., "Environmental stress affects the activity of metabolic and growth factor signaling networks and induces autophagy markers in MCF7 breast cancer cells", Molecular & Cellular Proteomics, 2014, 13(3), pp. 836-848.
Rajeeve et al., "Polyamine production is downstream and upstream of oncogenic PI3K signalling and contributes to tumour cell growth", Biochem J, 2013, 450, pp. 619-628.
Daub et al., "Kinase-Selective Enrichment Enables Quantitative Phosphoproteomics of the Kinome across the Cell Cycle", Cell, 2008, 31, pp. 438-448.
Miraki-Moud et al., "Arginine deprivation using pegylated arginine deiminase has activity against primary acute myeloid leukemia cells in vivo", Blood, 2015, 125(26), pp. 4060-4068.

(56) References Cited

OTHER PUBLICATIONS

Cox et al., "MaxQuant enables high peptide identification rates, individualized p.p.b.-range mass accuracies and proteome-wide protein quantification", Nature Biotechnology, 2008, 26(12), pp. 1367-1372.
Cascante et al., "Metabolic control analysis in drug discovery and disease", Nature Biotechnology, 2002, 20, pp. 243-249.
Smyth, "Limma: Linear Models for Microarray Data", Springer, New York, 2005, pp. 397-420.
Miller et al., "Mutations in the phosphatidylinositol 3-kinase pathway: role in tumor progression and therapeutic implications in breast cancer", Breast Cancer Research, 2011, 13(224), pp. 1-12.
Raynaud et al., "Pharmacologic Characterization of a Potent Inhibitor of Class I Phosphatidylinositide 3-Kinases", Cacner Res, 2007, 67(12), pp. 5840-5850.
Rajeeve et al., "Cross-species Proteomics Reveals Specific Modulation of Signaling in Cancer and Stromal Cells by Phosphoinositide 3-kinase (PI3K) Inhibitors", Molecular and Cellular Proteomics, 2014, 13.6, pp. 1457-1470.
Benjamini et al., "Controling the False Discovery Rate: A Practical and Powerful Approach to Multiple Testing", Journal of the Royal Statistical Society B, 1995, 57(1), pp. 289-300.
Huang et al., "Applcation of Pearson Correlation Coefficient (PCC) and Kolmogorov-Smirnov Distance (KSD) Metrics to Identify Disease Specific Biomarker Genes", BMC Bioinformatics, 2010, 11(suppl 4), pp. 1-2.
Alcolea et al., "In-Depth Analysis of Protein Phosphorylation by Multidimensionallon Exchange Chromatography and Mass Spectrometry", Meth Mol Biol, 2010, 658, pp. 111-126.
Alcolea et al., "Increased Confidence in Large-Scale Phosphoproteomics Data by Complementary Mass Spectrometric Techniques and Matching of Phosphopeptide Data Sets", J Proteome Res, 2009, 8(8), pp. 3808-3815.
Alessi et al., "Molecular Basis for the Substrate Specificity of Protein Kinase B; Comparison with MAPKAP Kinase-1 and p70 S6 Kinase", FEBS Lett, 1996, 399, pp. 333-338.
Bantscheff et al., "Quantitative Chemical Proteomics Reveals Mechanisms of Action of Clinical ABL Kinase Inhibitors", Nat Biotechnol, 2007, 25(9), pp. 1035-1044.
Barglow et al., "Activity-based protein profiling for the functional annotation of enzymes", Nat Methods, 2007, 4(10), pp. 822-827.
Blagoev et al., "Temporal Analysis of Phosphotyrosine-dependent Signaling Networks by Quantitative Proteomics" Nat Biotech, 2004, 22(9), pp. 1139-1145.
Blethrow et al., "Covalent capture of kinase-specific phosphopeptides reveals Cdk1-cyclin B substrates", PNAS, 2008, 105(5), pp. 1442-1447.
Bodenmiller et al. "Phosphoproteomic Analysis Reveals Interconnected System-Wide Responses to Perturbations of Kinases and Phosphatases in Yeast" Sci Signal, 2010, 3(153):rs4.
Cartlidge et al., "The IRNA Methylase METTL 1 is Phosphorylated and Inactivated by PKB and RSK in vitro and in Cells", Embo J, 2005, 24(9), pp. 1696-1705.
Casado et al., "A self-validating quantitative mass spectrometry method for assessing the accuracy of high-content phosphoproteomic experiments" Mol Cell Proteomics, 2011, 10(1):M110 003079.
Cutillas et al., "Biological signalling activity measurements using mass spectrometry", J Biochem, 2011, 434, pp. 189-199.
Cutillas et al., "Quantification of gel-separated proteins and their phosphorylation sites by LC-MS using unlabeled internal standards: analysis of phosphoprotein dynamics in a B cell lymphoma cell line" Molecular & cellular proteomics, 2005, 4(8), pp. 1038-1051.
Cutillas et al., "Quantitative profile for five murine core proteomnes using label-free functional proteomics" Mol Cell Proteomics, 2007, 6(9), pp. 1560-1573.
Cutillas et al., "Ultrasensitive and absolute quantification of the phosphoinositide 3-kinase/Akt signal transduction pathway by mass spectrometry", Proc Natl Acad Sci, 2006, 103(24), pp. 8959-8964.
Dayon et al., "Realative quantification of proteins in human cerebrospinal fluids by MS/MS using 6-plex isobaric tags" Anal Chem, 2008, 80(8), pp. 2921-2931.
Dinkel et al., "Phospho.ELM: a database of phosphorylation sites-update 2011", Nucleic Acids Res, 2011, 39, D261-D267.
Ficarro et al., "Automated immobilized metal affinity chromatography/nano-liquid chromatography/electrospray ionization mass spectrometry platform for profiling protein phosphorylation sites", Rapid Commun Mass Spcetom, 2005, 19(1), pp. 57-71.
Frewen et al., "Analysis of peptide MS/MS spectra from large-scale proteomics experiments using spectrum libraries", Anal Chem, 2006, 78, pp. 5678-5684.
Gerber et al., "Absolute quantification of proteins and phosphoproteins from cell lysates by tandem MS", PNAS, 2003, 100(12), pp. 6940-6945.
Gygi et al., "Quantitative analysis of complex protein mixtures using isotope-coded affinity tags", Nat Biotechnology, 1999, 17, pp. 994-999.
Hornbeck et al., "PhosphoSite: a bioinformatics resource dedicated to physiological protein phosphorylation", Proteomics, 2004, 4, pp. 1551-1561.
Huang et al., "Bioinformatics enrichment tools: paths toward the comprehensive functional analysis of large gene lists.", Nucleic Acids Research, 2009, 37(1), pp. 1-13.
Hummel et al., "ProMEX: a mass spectral reference database for proteins and protein phosphorylation sites", BMC Bioinformatics, 2007, 8, pp. 216.
Kirkpatrick et al., "The absolute quantification strategy: a general procedure for the quantification of proteins and post-translational modifications", Methods, 2005, 35(3), pp. 265-273.
Knebel et al., "A Novel Method to Identify Protein Kinase Substrates: eEF2 Kinase is Phosphorylated and Inhibited by SAPK4/p388", Embo J, 2001, 20(16), pp. 4360-4369.
Kubota et al., "Sensitive Multiplexed Analysis of Kinase Activities and Activity-based Kinase Identification", Nature Biotechnology, 2009, 27(10), pp. 933-940.
Luo et al., "Global Impact of Oncogenic Src on a Phosphotyrosine Proteome", J Proteome Res, 2008, 7, pp. 3447-3460.
Miller et al., "Linear Motif Atlas for Phosphorylation-Dependent Signaling", Sci Signal, 2008, 1(35):ra2.
Montoya et al., "Characterization of a TiO2 enrichment method for label-free quantitative phosphoproteomics", Methods, 2011, 54(4), pp. 370-378.
Nita-Lazar et al., "Quantitative phosphoproteomics by mass spectrometry: past, present, and future", Proteomics, 2008, 8(21), pp. 4433-4443.
Olsen et al., "Global, in vivo, and site-specific phosphorylation dynamics in signaling networks", Cell, 2006, 127, pp. 635-648.
Pasa-Tolic et al., "Proteomic analyses using an accurate mass and time tag strategy", Biotechniques, 2004, 37(4), pp. 621-624.
Perkins et al., "Probability-based protein identification by searching sequence databases using mass spectrometry data", Electrophoresis, 1999, 20, pp. 3551-3567.
Ross et al., "Multiplexed protein quantitation in *Saccharomyces cerevisiae* using amine-reactive isobaric tagging reagents", Mol Cell Proteomics, 2004, 3(12), pp. 1154-1169.
Ruse et al., "Quantitative dynamics of site-specific protein phosphorylation determined using liquid chromatography electrospray ionization mass spectrometry", Anal Chem, 2002, 74(7), pp. 1658-1664.
Savitski et al., "Confident Phosphorylation Site Localization Using the Mascot Delta Score", Technol In nov Resources, 2011, 10, pp. 1-12.
Schwartz et al., "An interative statistical approach to the identification of protein phosphorylation motifs from large-scale data sets", Nature Biotechnology, 2005, 23(11), pp. 1391.
Smith et al., "Recent developments in mass spectrometry-based quantitative phosphoproteomics", Biochem Cell Biol, 2008, 86(2), pp. 137-148.
Steen et al., "Stable isotope-free relative and absolute quantification of protein phosphorylation stoichiometry by MS", PNAS, 2005, 102(11), pp. 3948-3953.

(56) References Cited

OTHER PUBLICATIONS

Thingholm et al., "Analytical strategies for phosphoproteomics", Proteomics, 2009, 9, pp. 1451-1468.
Wang et al., "SEMI-quantitation Strategy for Label-free Quantitative Profiling of Phosphoproteome in Lung Cancer of Different Invasive Potential", Proceedings of the 56th ASMS Conference on Mass Spectrometry and Allied Topics, Denver, CO, Jun. 1-5, 2008.
Yang et al., "Applying a targeted label-free approach using LC-MS AMT tags to evaluate changes in protein phosphorylation following phosphatase inhibition", J Proteome Res, 2007, 6(11), pp. 4489-4497.
Yi et al., "Quantification of phosphorylation of insulin receptor substrate-1 by HPLC-ESI-MS/MS", J Am Soc Mass Spectrom, 2006, 17(4), pp. 562-567.
Yu et al., "A site-specific, multiplexed kinase activity assay using stable-isotope dilution and high-resolution mass spectometry", PNAS, 2009, 106(28), pp. 11606-11611.
Zhang et al., "Targeting cancer with small molecule kinase inhibitors" Nat Rev Cancer, 2009, 9(1), pp. 28-39.
Zhou et al., "A systematic approach to the analysis of protein phosphorylation", Nat Biotech, 2001, 19(4), pp. 375-378.
Glinski et al., "Stable isotope labeling of phosphopeptides for multiparallel kinase target analysis and identification of phosphorylation sites" Rapid Communications in Mass Spectrometry, 2003, 17, pp. 1579-1584.
Kirkpatrick et al., "Phosphoproteomic characterisation of DNA damage response in melanoma cells following MEK/PI3K dual inhibition", PNAS, 2013, 110(48), pp. 19426-19431.
Cutillas, "Deep analysis of signalling plasticity in a breast cancer kinase network during acquisition of resistance to PI3K and mTORC1/2 inhibitors", NCI Cancer Conference, Nov. 4, 2013, Liverpool.
Non-Final Office Action dated Jan. 22, 2021 in related U.S. Appl. No. 15/579,363.
Final Office Action dated May 26, 2021 in related U.S. Appl. No. 15/579,363.
U.S. Appl. No. 14/384,151, filed Sep. 9, 2014 which is the National Stage Entry of PCT Application No. PCT/EP2013/054764, filed Mar. 8, 2013.
U.S. Appl. No. 15/579,363, filed Dec. 4, 2017 which is the National Stage Entry of PCT Application No. PCT/GB16/51639, filed Jun. 3, 2016.

* cited by examiner

METHOD FOR PROTEIN KINASE ACTIVITY RANKING

CROSS-REFERENCE TO RELATED APPLICATIONS

This application is a 35 U.S.C. § 371 national phase application of PCT Application No. PCT/EP16/77845, filed Nov. 16, 2016, which claims priority to Great Britain Application No. 1520178.3, filed Nov. 16, 2015, each of which is incorporated herein by reference in its entirety.

FIELD OF THE INVENTION

The present invention relates to a method of quantifying the activity of a protein modifying enzyme in a sample, and finds particular use in the quantification of the activity of a protein kinase. The method can be used to determine the most suitable inhibitor of a protein modifying enzyme, for example a kinase inhibitor, with which to treat a patient and is therefore useful in the field of personalized medicine.

BACKGROUND TO THE INVENTION

Protein kinases control the activity of cell signalling pathways that in turn regulate key biological functions, including migration, metabolism and proliferation. Cell signalling pathways form complex networks of biochemical reactions that integrate and decode extracellular signals into appropriate cellular responses. Reconstructing these networks, and systematic analysis of their properties, is important to advance our molecular understanding of disease at the systems level. The importance of such pathways in the regulation of cell biology is underscored by the fact that kinases are deregulated in a wide array of diseases; examples include AMP activated kinase (AMPK) in diabetes, Janus kinase (JAK) in auto-inflammatory conditions, GSK3β in neurodegeneration and Akt in different forms of cancer.

There are more than 500 kinase genes in humans with just about 200 of these expressed in a given cell population. Despite much research in this area, methods to quantify the contribution of each of these kinases to the global signalling output are lacking. Indeed, all methods currently used to quantify signalling (which are based on either mass spectrometry (MS) or immunochemical techniques) assess the activity of a given signalling pathway relative to a control or to another sample. For example, the inventors' earlier application published as WO 2013/132075 relates to a method of quantifying the activity of a protein modifying enzyme in a sample by analysing modified peptides from different samples. This is termed Kinase Substrate Enrichment Analysis (KSEA), and is also disclosed in Casado et al Science Signaling 6, rs6 (2013).

These methods are therefore useful to investigate how signalling is modulated across different conditions, but these cannot be used to rank kinases based on how much they contribute to signalling relative to each other within a given cell population.

The inability of the state-of-the-art techniques to rank kinases within a cell population or tissue based on how much they contribute to a given phenotype constitutes a well-known clinical problem. Inhibitors of kinases are effective for some cancer patients but a significant number of them do not respond to such drugs. In some instances genetic or protein markers are used for personalizing cancer therapies, but the accuracy of current biomarkers of responses is often low. This hampers the development of personalized medicine.

The variability of responses of cancers to kinase therapies is probably due to the fact that cancers are biologically heterogeneous. Indeed, efforts to identify a set of essential kinases commonly activated in all cancer patients have instead revealed that the wiring of kinase proliferative networks varies significantly between cells taken from different patients. Therefore, cancer cells exhibit tremendous variation in their kinase requirements for proliferation. The practical consequence of this heterogeneity is that patients respond to kinase inhibitors to different extents. For example, about 50% of melanomas harbour the V600E mutation on the BRAF protein kinase; 50% of these responded well to vemurafenib, an inhibitor of mutated BRAF, i.e., a 25% overall response. Similarly, about 30% of breast cancers have mutations on PIK3CA, the gene coding for the p110α isoform of PI3K. A recent clinical trial showed that ~30% of patients positive for PIK3CA mutations responded to PI3K inhibitors according to defined criteria; a 10% overall response. At present it is not known why patients positive for a given mutation respond variably to kinase specific inhibition of the mutated target; and the identity of pathways that drive the malignant phenotype of tumours without mutations on these genes is also not known for most patients.

There is therefore a need in the art to quantifying the activity of protein modifying enzymes such as kinases within a particular sample in order to allow the determination of the most suitable therapy with which to treat a patient.

SUMMARY OF THE INVENTION

The present inventors have developed two algorithms to quantify the contribution of individual protein modifying enzymes (such as protein kinases) in a given cell population to cell signalling. The output of these algorithms can be used to rationally select the most appropriate cell signalling inhibitor to treat individual patients. The outputs of the algorithms are termed Kinase Activity Ranking (KAR) and "Sensitivity Coefficient" (SC) respectively. The output of KAR is an index of kinase activity which termed "K-Score" (referred to as K herein).

Accordingly, in a first aspect, the present invention provides a method of quantifying the activity of a protein modifying enzyme in a sample, comprising calculating the value K for said protein-modifying enzyme as follows:

$$K = \frac{\sum_{i=1}^{m} \alpha_i}{\sum_{j=1}^{l} \beta_j}$$

wherein
m=the number of modified peptides in the sample that are substrates of said protein modifying enzyme;
α=the intensity of the modified peptides i;
i=each modified peptide in the sample that is a substrate of said protein modifying enzyme;
l=the total number of modified peptides in the sample;
β=the intensity of the modified peptides j; and
j=all of the modified peptides in the sample.

In a further aspect, the present invention provides a method of quantifying the activity of a protein modifying enzyme in a sample, comprising calculating the value SC for said protein-modifying enzyme as follows:

$$SC = -\log_2\left(\frac{P_{Ci}}{C_i} \cdot IC_{50i}\right)$$

wherein $P_{Ci}$=reduction in proliferation using inhibitor at $C_i$;
$C_i$=inhibitor concentration at which proliferation is measured; and
$IC_{50i}$="in vitro" $IC_{50}$ of inhibitor against primary target.

Viewed alternatively, the present disclosure describes a method of determining the level of activity of a protein modifying enzyme in a sample, comprising
(i) determining the total number of modified peptides in the sample;
(ii) determining the intensity of the modified peptides;
(iii) determining the number of modified peptides in the sample that are substrates of said protein modifying enzyme;
(iv) determining the intensity of the modified peptides that are substrates of said protein modifying enzyme
calculating the value K for said protein-modifying enzyme as follows:

$$K = \frac{\sum_{i=1}^{m} \alpha_i}{\sum_{j=1}^{l} \beta_j}$$

wherein
m=the number of modified peptides in the sample that are substrates of said protein modifying enzyme;
α=the intensity of the modified peptides i;
i=each modified peptide in the sample that is a substrate of said protein modifying enzyme;
l=the total number of modified peptides in the sample;
β=the intensity of the modified peptides j; and
j=all of the modified peptides in the sample
wherein the K value is directly proportional to the level of activity of said protein modifying enzyme.

DETAILED DESCRIPTION OF THE INVENTION

The present invention relates to methods for quantifying the activity of a protein modifying enzyme such as a protein kinase in a sample. The methods are based on the analysis of modified peptides, for example phosphorylated peptides, which are typically identified in the first aspect of the invention using MS-based techniques.

As described herein, the methods of the invention are methods for quantifying the activity of a protein modifying enzyme in a sample. Most proteins are modified in some way by the addition of functional groups and such modifications are effected by protein modifying enzymes. Protein modifications that can be detected by mass spectrometry include phosphorylation, glycosylation, acetylation, methylation and lipidation. These protein modifications have various biological roles in the cell. The modification sites may therefore be sites of post-translational modifications. For example, the modification sites may be sites may be sites of phosphorylation, glycosylation, acetylation, methylation and lipidation. The modification sites are typically protein and/or peptide modification sites. A modification site may be one or more amino acid residues of a peptide or protein to which a functional group such as a phosphate group is added to the peptide or protein. Alternative functional groups include carbohydrates, acetyl groups, methyl groups and lipids. By "protein modifying enzyme" is therefore meant an enzyme which catalyses a reaction involving the addition of a functional group to a protein or peptide. A "modified peptide" is defined herein as a peptide which has been modified by the addition or removal of a functional group. A "protein modifying enzyme" is defined herein as an enzyme which catalyses a reaction involving the addition or removal of a functional group to a protein or peptide.

The methods of the invention can be applied to the quantification of the activity of any protein modifying enzyme whose activity can be detected using MS-based methods. Such enzymes include protein kinases (also referred to herein as "kinases"), protein glycosyltransferases, protein acetyltransferases, protein methyltransferases and protein palmitoyltransferases. The activity of these enzymes results in phosphorylation, acetylation, glycosylation, methylation and lipidation of protein or peptide substrates respectively. All of these protein modifications can be detected by mass spectrometry.

The methods of the invention are based on the analysis of modified peptides. Modified peptides contain one or more amino acid which has been modified, for example phosphorylated, acetylated, glycosylated, methylated or lipidated, by a protein modifying enzyme. Such modified amino acids are referred to herein as "modification sites". When a modified peptide is modified by a particular protein modifying enzyme, it is referred to as a "substrate" of that enzyme. The modified peptide includes one or more amino acid which has been modified by the protein modifying enzyme.

In one embodiment, the method of the invention is a method of quantifying the activity of a protein kinase. In this embodiment, the method is based on the analysis of phosphorylated peptides. Phosphorylated peptides contain one or more amino acid which is phosphorylated (i.e. a phosphate ($PO_4$) group has been added to that amino acid). Such phosphorylated amino acids are referred to herein as "phosphorylation sites". When a peptide is phosphorylated by a particular protein kinase, it is referred to as a "substrate" of that protein kinase. In relation to this embodiment of the invention, the term "phosphoprotein" is used herein to refer to a phosphorylated protein and the term "phosphopeptide" is used herein to refer to a phosphorylated peptide.

Human protein kinases can be divided into a number of groups including AGC kinases, for example protein kinase A (PKA), protein kinase B (PKB) (also known as Akt), protein kinase C (PKC) and protein kinase G (PKG); tyrosine kinases; tyrosine-kinase like kinases; calcium/calmodulin-dependent protein kinases; the casein kinase 1 group; CMGC group, for example CDK, MAPK, GSK3 and CLK kinases; and STE, the homologues of yeast Sterile 7, Sterile 11, and Sterile 20 kinases.

The methods of the invention are methods of quantifying the activity of a protein modifying enzyme in a sample. The sample used in the methods of the invention can be any sample which contains peptides. The sample is typically a biological sample and can thus be any type of sample obtained from a biological source, for example a sample obtained from a human, animal, plant or bacterium. The invention thus encompasses the use of samples obtained from human and non-human sources.

The samples used in the methods of the present invention can be from any species of interest. Typically, the samples are from a human or animal. The animal is typically a mammal, for example a rodent such as a mouse, rat or guinea pig, or an ungulate such as a cow, sheep or goat. The animal is alternatively a bird, such as a chicken, a fish, such as a zebra fish, a nematode, such as the worm *Caenorhabditis elegans*, or an insect, such as the fruit fly *Drosophila melanogaster*. The samples used in the methods of the invention can also be from other life-forms such as bacteria and yeast. The samples used in the methods of the invention are typically samples from an experimentally important species of bacterium such as *Escherichia coli, Salmonella enterica, Streptococcus pneumoniae* or *Staphylococcus aureus*, or of yeast such as the baker's yeast *Saccharomyces cerevisiae* or the fission yeast *Schizosaccharomyces pombe*. The samples used in the methods of the invention can alternatively be from a plant or fungus or a virus.

The present invention finds use in the field of personalized medicine. Typically, therefore, the biological sample is derived from a human, and can be, for example, a sample of a bodily fluid such as urine or blood, or another tissue. Typically, the biological sample is a cell line or a tissue, typically a primary tissue. For example, the sample can be a tissue from a human or animal. The human or animal can be healthy or diseased. In an embodiment, the human has been diagnosed with or is suspected as having cancer, for example lymphoma or leukemia, for example acute myeloid leukemia (AML). Accordingly, the tissue may be cancer tissue. For example, the sample may be from a tumour. Alternatively, the sample can be a cell line derived from healthy or diseased human or animal cells.

The first and second samples used in the method of the invention typically are or include cells from cell lines, for example a cancer cell line such as a breast cancer cell line, for example an MCF7 cell line. Many cancer cell lines are known in the art and are listed online, for example in the Broad-Novartis Cancer Cell Line Encyclopedia (CCLE) found on the world wide web at broadinstitute.org/ccle/home The first and second samples are typically from the same cell line but may be different. The first and second samples may be derived from the same source. For example, the first and second samples may both be from a single individual. The first and second samples may be from the same tissue. The first and second samples may be from the same bodily fluid.

A sample may be referred to herein as a "test sample" in order to distinguish the sample from another sample used in a method of the invention. For example, a sample may be referred to as a test sample in order describe a method involving a comparison with a control sample.

The methods of the invention are in vitro methods and therefore do not comprise the step of obtaining a sample from an organism such as an animal.

The modified peptides may be modified in the sample. The modified peptides may be modified in vivo. The modified peptides may be endogenous modified peptides.

The method of the first aspect of the invention is a method of quantifying the activity of a protein modifying enzyme in a sample, comprising calculating the value K for said protein-modifying enzyme as follows:

$$K = \frac{\sum_{i=1}^{m} \alpha_i}{\sum_{j=1}^{l} \beta_j}$$

The value K is the sum of the intensities of all modified peptides known to be substrates of a given protein modifying enzyme divided by the sum of the intensities of all modified peptides present in a sample. As the person skilled in the art will understand, the "intensity" of a peptide corresponds to its abundance, for example in a sample. Intensities can be calculated, for example, using peak areas or height of chromatograms from LC-MS data.

In the formula set out above, m=the number of modified peptides in the sample that are substrates of the protein modifying enzyme whose activity is being quantified; α=the intensity of the modified peptides i, wherein i=each modified peptide in the sample that is a substrate of said protein modifying enzyme; l=the total number of modified peptides in the sample; and β=the intensity of the modified peptides j, wherein j=all of the modified peptides in the sample.

In some embodiments, the intensities of the modified peptides i and j are normalized. Normalization is typically carried out relative to the total intensity.

In some embodiments, a correction factor is used to take account of the fact that some kinases have a larger number of substrates than others, and that more information is known on kinase-substrate relationships for better known kinases. In these embodiments, the value K is calculated for said protein-modifying enzyme as follows:

$$K = \frac{\sum_{i=1}^{m} \alpha_i}{\sum_{j=1}^{l} \beta_j} \cdot \left(\frac{m}{t}\right)^{1/2}$$

wherein
t=the total number of known target modified peptides for said protein modifying enzyme.

Conveniently, a multiplication factor can be used to bring the figure for the value K to a more manageable level. For example, a multiplication factor of $10^2$, $10^4$ or $10^6$ can be used. Where a multiplication factor of $10^6$ is used the value K is calculated as follows:

$$K = \frac{\sum_{i=1}^{m} \alpha_i}{\sum_{j=1}^{l} \beta_j} \cdot \left(\frac{m}{t}\right)^{1/2} \cdot 10^6$$

The method of the first aspect of the invention involves determining the number of modified peptides in the sample that are substrates of a particular protein modifying enzyme. In other words, the method involves determining the number of modified peptides that have a modification site that is modified by the same protein modifying enzyme. Thus, each of these modified peptides has at least one modification site that is modified by the same protein modifying enzyme. For example, when the activity of a protein kinase is being analysed, the method involves determining the number of phosphorylated peptides that they have a phosphorylation site that is phosphorylated by the same kinase. In this embodiment, a phosphorylation site within each of the phosphorylated peptides is known to be phosphorylated by the same kinase. Similarly, if the protein modifying enzyme is an acetylase, the method involves determining the number of modified peptides that have an acetylation site that is acetylated by the same acetylase. In this embodiment, an acetylation site within each of the acetylated peptides is known to be acetylated by the same specific acetylase.

Information on kinase-substrate relationships and therefore on phosphorylation sites that are phosphorylated by a particular kinase can be obtained from publically available databases, for example PhosphoSite (Hornbeck et al, Proteomics 4, 1551 (June 2004)), PhosphoSitePlus (found on the world wide web at phosphosite.org/) and PhosphoElm (Dinkel et al, *Nucleic Acids Res* 39, D261 (January 2011)). Similarly, information on other modification sites can be obtained experimentally or from publically available databases and from individual research papers obtained from the literature.

In some embodiments of the invention, the sample itself or the organism from which the sample is obtained is treated with a test substance prior to carrying out the method of the invention. Thus, in this embodiment, a cell line or an organism from which a tissue is obtained is treated with a test substance prior to carrying out the method of the invention. The test substance is typically an exogenous chemical or drug, such as small molecule inhibitors, RNAi, therapeutic peptides, and antibodies. This embodiment of the invention allows the investigation of the effects of the test substance on the activity of a protein modifying enzyme.

For example, in one embodiment, a cell line can be treated with agonists of pathways and/or kinase inhibitors prior to carrying out the method of the invention. Typical kinase inhibitors include inhibitors of src and phosphoinositide 3-kinase (PI3K), such as PP2 and PI-103. Other inhibitors of PI3K include wortmannin. At least 80 kinase inhibitors are in different stages of clinical development (Zhang, J.; et al *Nat Rev Cancer* 2009, 9, (1), 28-39). The technique is also useful to investigate other types of inhibitors suspected to have an effect on kinase pathways, such as HSP90 inhibitors, phosphatase inhibitors and antibody drugs.

A "peptide" as defined herein is a short amino acid sequence and includes oligopeptides and polypeptides. Typically, such peptides are between about 5 and 30 amino acids long, for example from 6 or 7 to 25, 26 or 27 amino acids, from 8, 9 or 10 to 20 amino acids, from 11 or 12 to 18 amino acids or from 14 to 16 amino acids, for example 15 amino acids. However, shorter and longer peptides, such as between about 2 and about 50, for example from about 3 to about 35 or 40 or from about 4 to about 45 amino acids can also be used. Typically, the peptide is suitable for mass spectrometric analysis, that is the length of the peptide is such that the peptide is suitable for mass spectrometric analysis. The length of the peptide that can be analysed is limited by the ability of the mass spectrometer to sequence such long peptides. In certain cases polypeptides of up to 300 amino acids can be analysed, for example from 50 to 250 amino acids, from 100 to 200 amino acids or from 150 to 175 amino acids.

As described herein, the method of the first aspect of the invention is based on the analysis of modified peptides which are identified and/or quantified in one embodiment of the invention using MS-based techniques. In some embodiments, the method of the first aspect of the invention therefore includes a step of identifying and/or quantifying modified peptides in a sample using mass spectrometry (MS), prior to calculating the value K for the protein-modifying enzyme of interest. In this embodiment, the invention provides a method of quantifying the activity of a protein modifying enzyme in a sample, comprising identifying and/or quantifying modified peptides using mass spectrometry (MS) and calculating the value K for said protein-modifying enzyme as follows:

$$K = \frac{\sum_{i=1}^{m} \alpha_i}{\sum_{j=1}^{l} \beta_j}$$

wherein
m=the number of modified peptides in the sample that are substrates of said protein modifying enzyme;
α=the intensity of the modified peptides i;
i=each modified peptide in the sample that is a substrate of said protein modifying enzyme;
l=the total number of modified peptides in the sample;
β=the intensity of the modified peptides j;
j=all of the modified peptides in the sample.

Identification and/or quantification of modified peptides can be carried out using any suitable method. Typically, identification and/or quantification can be carried out by any method involving mass spectrometry (MS), such as liquid chromatography-mass spectrometry (LC-MS). The LC-MS or LC-MS/MS is typically label-free MS but techniques that use isotope labelling as the basis for identification and/or quantification can also be used as the basis for the analysis.

In the methods of the present invention, identification and/or quantification of a protein modification such as phosphorylation is typically carried out using the TIQUAS (targeted and in-depth quantification of signalling) technique, as described in WO 2010/119261 (International patent application no. PCT/GB2010/000770) and incorporated herein in its entirety by reference. This technique allows for sensitive, rapid and comprehensive quantification of modified peptides. The method can, in one simple assay, simultaneously measure the amounts of thousands of phosphorylation sites on proteins. As set out in WO 2010/119261, the TIQUAS technique can also be used to quantify modified peptides other than phosphorylated peptides. In fact, the TIQUAS technique can be used to quantify peptides which contain any modifications which can be detected by mass spectrometry.

In this embodiment of the method of the first aspect of the invention, the step of identifying and/or quantifying modified peptides using mass spectrometry (MS) prior to calculating the value K for said protein-modifying enzyme is carried out using a method comprising the following steps:
  (a) obtaining peptides from a sample;
  (b) adding reference modified peptides to the peptides obtained in step (a) to produce a mixture of peptides and reference modified peptides;
  (c) carrying out mass spectrometry (MS) on said mixture of peptides and reference modified peptides to obtain data relating to the peptides in the sample; and
  (d) comparing the data relating to the peptides in the sample with data in a database of modified peptides using a computer programme;
wherein the database of modified peptides is compiled by a method comprising:
  i obtaining peptides from a sample;
  ii enriching modified peptides from the peptides obtained in step i;
  iii carrying out liquid chromatography-tandem mass spectrometry (LC-MS/MS) on the enriched modified peptides obtained in step ii;
  iv comparing the modified peptides detected in step iii to a known reference database in order to identify the modified peptides; and
  v compiling data relating to the modified peptides identified in step iv into a database.

In one embodiment of the method of the first aspect of the invention, where the protein modifying enzyme is a protein kinase and the modification is phosphorylation, the step of identifying and/or quantifying modified peptides using mass spectrometry (MS) prior to calculating the value K for said protein kinase is carried out using a method comprising the following steps:
(a) obtaining phosphorylated peptides from a sample;
(b) adding reference phosphorylated peptides to the peptides obtained in step
(a) to produce a mixture of phosphorylated peptides and reference phosphorylated peptides;
(c) carrying out mass spectrometry (MS) on said mixture of phosphorylated peptides and reference phosphorylated peptides to obtain data relating to the phosphorylated peptides in the sample; and
(d) comparing the data relating to the phosphorylated peptides in the sample with data in a database of phosphorylated peptides using a computer programme;
wherein the database of phosphorylated peptides is compiled by a method comprising:
i obtaining peptides from a sample;
ii enriching phosphorylated peptides from the peptides obtained in step i;
iii carrying out liquid chromatography-tandem mass spectrometry (LC-MS/MS) on the enriched phosphorylated peptides obtained in step ii;
iv comparing the phosphorylated peptides detected in step iii to a known reference database in order to identify the phosphorylated peptides; and
v compiling data relating to the phosphorylated peptides identified in step iv into a database.

In relation to this embodiment of the invention, the work "peptide" is used interchangeably with the word "polypeptide".

Step (a) of this embodiment of the invention involves obtaining peptides from a sample. Peptides can be obtained from the sample using any suitable method known in the art. In one embodiment, step (a) of the method of the invention comprises:
(1) lysing cells in the sample;
(2) extracting the proteins from the lysed cells obtained in step (1); and
(3) cleaving said proteins into peptides.

In step (1) of this embodiment of the invention, the cells in the sample are lysed, or split open. The cells can be lysed using any suitable means known in the art, for example using physical methods such as mechanical lysis (for example using a Waring blender), liquid homogenization, sonication or manual lysis (for example using a pestle and mortar) or detergent-based methods such as CHAPS or Triton-X. Typically, the cells are lysed using a denaturing buffer such as a urea-based buffer.

In step (2) of this embodiment of the invention, proteins are extracted from the lysed cells obtained in step (1). In other words, the proteins are separated from the other components of the lysed cells. In step (3) of this embodiment of the invention, the proteins from the lysed cells are cleaved into peptides. In other words, the proteins are broken down into shorter peptides. Protein breakdown is also commonly referred to as digestion. Protein cleavage can be carried out in the present invention using any suitable agent known in the art.

Protein cleavage or digestion is typically carried out using a protease. Any suitable protease can be used in the present invention. In the present invention, the protease is typically trypsin, chymotrypsin, Arg-C, pepsin, V8, Lys-C, Asp-C and/or AspN. Alternatively, the proteins can be cleaved chemically, for example using hydroxylamine, formic acid, cyanogen bromide, BNPS-skatole, 2-nitro-5-thiocyanobenzoic acid (NTCB) or any other suitable agent.

In step (b) of this embodiment, reference modified peptides (typically reference phosphorylated peptides) are added to the peptides obtained in step (a) to produce a mixture of peptides and reference modified peptides (typically reference phosphorylated peptides). Step (b) thus results in one mixture of peptides (including modified ones, typically phosphorylated ones) per sample. The reference modified peptides (typically reference phosphorylated peptides) are also referred to herein as "internal standards" (ISs). Typically, 5 to 10, for example 6 to 9 or 7 to 8, reference modified peptides (typically reference phosphorylated peptides) are added.

In the present invention, the reference modified peptides are typically reference phosphorylated peptides and are typically derived from a reference protein of defined nature and concentration, often referred to as an internal standard (IS) protein. ISs can be commercially available proteins, for example casein. Alternatively, ISs are synthesised specifically for use in the invention. In this embodiment of the invention, reference phosphorylated peptides are typically synthesised with the same sequence as some of the phosphorylated peptides that it is desired to quantify but which are enriched in stable heavy isotopes of carbon and nitrogen. The peptides are typically synthesised using solid phase chemistry in which one amino acid is added at a time to form an amino acid chain or polypeptide. Typically, such peptides are enriched in $^{13}C$ and $^{15}N$ that substitute the common $^{12}C$ and $^{14}N$. This enrichment results in the reference phosphorylated peptides being approximately 6 to 10 daltons heavier than the endogenous phosphorylated peptides with the same sequence so that they can be distinguished using a mass spectrometer.

In another embodiment of the invention, when the protein modifying enzyme is a protein acetyltransferase and acetylated peptides are being quantified, the reference modified peptides are reference acetylated peptides. Such reference acetylated peptides are typically synthetic peptides containing acetylated amino acids.

The reference modified peptides (typically reference phosphorylated peptides) are typically added at a known amount in each of the samples to be compared. The signals of the endogenous modified peptides (typically phosphorylated peptides) are normalised to the signal of the reference modified peptides (typically reference phosphorylated peptides) in downstream analysis.

In one embodiment, step (b) of this embodiment further comprises enriching modified peptides (typically phosphorylated peptides) from the mixture of peptides and reference modified peptides (typically reference phosphorylated peptides) obtained in step (b) to produce a mixture of enriched modified peptides (typically phosphorylated peptides). This additional step thus results in a single mixture of enriched modified peptides (typically phosphorylated peptides) per sample. In this embodiment of the invention, step (c) thus comprises carrying out mass spectrometry (MS) on the mixture of enriched modified peptides (typically phosphorylated peptides) to obtain data relating to the peptides in the sample. In this embodiment of the invention, step (b) typically results in a mixture of enriched modified peptides (typically phosphorylated peptides).

The step of enriching modified peptides (typically phosphorylated peptides) is typically carried out using chromatography. In one embodiment, the chromatography is immobilized metal ion affinity chromatography (IMAC), titanium dioxide (TiO$_2$) chromatography, and/or zirconium dioxide (ZrO$_2$) chromatography. Typically, the chromatography is IMAC and TiO$_2$ chromatography.

Alternatively, the step of enriching modified peptides (typically phosphorylated peptides) is carried out using antibody-based methods.

In one embodiment of the invention, when the protein modifying enzyme is a protein kinase and the peptides being identified and/or quantified are phosphorylated peptides, antibodies with affinity to phosphorylated amino acids such as tyrosine, threonine, serine or histidine are linked (immobilised) to a solid matrix. Phosphorylated peptides are enriched by the ability of these antibodies to specifically bind phosphorylated peptides. Non-phosphorylated peptides are then washed away while phosphorylated peptides are retained on the antibody coated matrices. Elution of phosphorylated peptides from the immobilised antibody is typically carried out using low pH solvents or by any other suitable method that denatures the interaction between antibody and phosphorylated peptides.

In another embodiment of the invention, when the protein modifying enzyme is a protein acetyltransferase and the peptides being identified and/or quantified are acetylated peptides, acetylated peptides are enriched by the use of specific antibodies against acetylated amino acid residues. Such antibodies are linked to a solid matrix and then enriched by the ability of the antibodies to specifically bind acetylated amino acid residues. Non-acetylated peptides are then washed away while acetylated peptides are retained on the immobilised antibody.

In step (c) of this embodiment, mass spectrometry (MS) is carried out on the mixture of peptides and reference modified peptides (typically reference phosphorylated peptides) obtained in step (b) to obtain data relating to the peptides in the sample. Typically, this data is in the form of an MS datafile for the sample. In one embodiment of the invention, when step (b) of this embodiment further comprises enriching modified peptides (typically phosphorylated peptides) from the mixture of peptides and reference modified peptides (typically reference phosphorylated peptides) obtained in step (b) to produce a mixture of enriched modified peptides (typically phosphorylated peptides), step (c) comprises carrying out mass spectrometry (MS) on said mixture of enriched modified peptides (typically phosphorylated peptides) to obtain data relating to the peptides in the sample, typically an MS datafile for the sample. Typically, the mass spectrometry is liquid chromatography-mass spectrometry (LC-MS). Step (c) thus typically results in an LC-MS datafile (one from each sample).

The data relating to the peptides in the sample typically comprises the mass to charge (m/z) ratio, charge (z) and/or relative retention time of the peptides.

In step (d) of this embodiment, the data relating to the peptides in the sample (typically in the form of an MS datafile and more typically an LC-MS datafile) is compared with data in a database of modified peptides (typically phosphorylated peptides) using a computer programme. For example, the mass to charge (m/z) ratio, charge (z) and relative retention time of the peptides in the sample are compared with the mass to charge (m/z) ratio, charge (z) and relative retention time of the modified peptides (typically phosphorylated peptides) in the database. This enables the identification and quantification of each modified peptide (typically phosphorylated peptide) in the sample using the database of modified peptides (typically phosphorylated peptides).

Typically, the computer programme is the programme termed PESCAL (Cutillas, P. R.; Vanhaesebroeck, B. *Mol Cell* Proteomics 6(9), 1560-73, 2007). PESCAL constructs extracted ion chromatograms (XIC, i.e, an elution profile) for each of the modified peptides (typically phosphorylated peptides) present in the database across all the samples that are to be compared. This is done by centring the XIC on the m/z and retention time of the peptide previously identified to be modified (typically phosphorylated) (i.e, present in the database constructed in the first step of the procedure). PESCAL also considers the charge of the peptide to help in the correct assignment of identity. The program also calculates the peak height and area under the curve of each XIC. The data is normalised by dividing the intensity reading (peak areas or heights) of each modified peptides (typically phosphorylated peptide) that is being analysed by those of the reference modified peptides (typically reference phosphorylated peptides).

In this embodiment, the database of modified peptides is compiled by a method comprising the following steps:
  i obtaining peptides from a sample;
  ii enriching modified peptides from the peptides obtained in step i;
  iii carrying out liquid chromatography-tandem mass spectrometry (LC-MS/MS) on the enriched modified peptides obtained in step ii;
  iv comparing the modified peptides detected in step iii to a known reference database in order to identify the modified peptides; and
  v compiling data relating to the modified peptides identified in step iv into a database.

Other computer programmes and workflows, such as MaxQuant [Nature Biotechnology 26, 1367-1372 (2008)] may be used to quantify peptides and these are compatible with the present invention.

Step i of this embodiment involves obtaining peptides from a sample. Peptides can be obtained from the sample using any suitable method known in the art and as described herein. The sample of step i may be a third sample.

The sample is typically a biological sample and can thus be any type of sample obtained from a biological source, as described above. Typically, the sample is a cell line or a tissue.

In some embodiments of the invention, where the sample used in step i is a cell line, the sample may be treated with an inhibitor prior to carrying out step i. The inhibitor can be any suitable type of inhibitor. Typically, when phosphorylated peptides are being identified and/or quantified, the inhibitor is a phosphatase inhibitor. Treatment with phosphatase inhibitors increases the stoichiometry of phosphorylation and results in a greater number of phosphorylated peptides that can be included in the database. In addition, methyl transferase or acetyl hydrolase inhibitors can be used when the purpose is to identify and/or quantify methylated and acetylated peptides, respectively.

In one embodiment, step i of this embodiment of the method of the invention comprises:
  (1) lysing cells in a sample;
  (2) extracting the proteins from the lysed cells obtained in step (1); and
  (3) cleaving said proteins into peptides.

These aspects of the invention are as described above. However, step (3) is typically carried out using the same method as in step (a) described above.

In step ii of this embodiment, modified peptides (typically phosphorylated peptides) are enriched from the peptides obtained in step i. Step ii thus results in several fractions enriched in modified peptides (typically phosphorylated peptides).

The enrichment of modified peptides (typically phosphorylated peptides) in step ii is typically carried out using multidimensional chromatography. In one embodiment, the multidimensional chromatography is carried out using strong cation exchange high performance liquid chromatography (SCX-HPLC), immobilized metal ion affinity chromatography (IMAC) and titanium dioxide ($TiO_2$) chromatography. In another embodiment, the multidimensional chromatography is carried out using anion exchange high performance liquid chromatography (SAX-HPLC), immobilized metal ion affinity chromatography (IMAC) and titanium dioxide ($TiO_2$) chromatography. In these embodiments of the invention, the chromatographical techniques are carried out sequentially.

Alternatively, the enrichment of modified peptides (typically phosphorylated peptides) in step ii is carried out using antibody-based methods, as described above.

In step iii of this embodiment, liquid chromatography-tandem mass spectrometry (LC-MS/MS) is carried out on the enriched modified peptides (typically phosphorylated peptides) obtained in step ii. In step iv of this embodiment, the modified peptides (typically phosphorylated peptides) detected in step iii are compared to a known reference database in order to identify the modified peptides (typically phosphorylated peptides). This step is typically carried out using a commercially available search engine, such as, but not restricted to, the MASCOT, ProteinProspector, Andromeda, or Sequest search engines.

In step v of this embodiment, data relating to the modified peptides (typically phosphorylated peptides) identified in step iv is compiled into a database. This database lists all the parameters needed for the quantification of phosphorylated peptides in subsequent biological experiments. Typically, the data relating to the modified peptides (typically phosphorylated peptides) includes identity of the modified peptides (typically phosphorylated peptide), mass to charge (m/z) ratio, charge and/or relative retention time. This allows data relating to the peptides in the sample, typically the mass to charge (m/z) ratio, charge (z) and relative retention time of the peptides in the sample, to be compared to the values for the modified peptides (typically phosphorylated peptides) in the database and thus allows the identification and quantification of the modified peptides (typically phosphorylated peptides) in the sample.

In this embodiment, the compilation of the database does not need to be carried out simultaneously with the method of the invention. The compilation of the database can be carried out separately, in advance of the TIQUAS technique being used in the method of the invention to identify and/or quantify the peptide in the sample.

The basis of the TIQUAS technique is the construction of a database of modified peptides (typically phosphorylated peptides) that can be detected and quantified by LC-MS. This database lists all the parameters needed for the quantification of modified peptides (typically phosphorylated peptides) in subsequent biological experiments including the identity of the modified peptide (typically phosphorylated peptide), mass to charge ratio (m/z), charge, and relative retention time. The database can be constructed by enriching modified peptides (typically phosphorylated peptides) using multidimensional chromatography (such as strong cation exchange, IMAC and $TiO_2$). Fractions of enriched modified peptides (typically phosphorylated peptides) can then be analysed by LC-MS/MS for identification of modified peptides (typically phosphorylated peptides).

The computer program named PESCAL (Cutillas and Vanhaesebroeck, *Molecular & Cellular Proteomics* 6, 1560-1573 (2007)) automates the quantification of each of the modified peptides (typically phosphorylated peptides) listed in the database in LC-MS runs of modified peptides (typically phosphorylated peptides) taken from biological experiments. For these biological experiments, proteins in cell lysates are digested using trypsin or other suitable proteases. Peptide (such as phosphopeptide) internal standards, which are reference modified peptides (typically reference phosphorylated peptides), are spiked at known amounts in all the samples to be compared. Modified peptides (typically phosphorylated peptides) in the resultant peptide mixture are enriched using a simple-to-perform IMAC or $TiO_2$ extraction step. Enriched modified peptides (typically phosphorylated peptides) are analysed in a single LC-MS run of typically but not restricted to about 120 minutes (total cycle). PESCAL then constructs extracted ion chromatograms (XIC, i.e, an elution profile) for each of the modified peptides (typically phosphorylated peptides) present in the database across all the samples that are to be compared. The program also calculates the peak height and area under the curve of each XIC. The data is normalised by dividing the intensity reading (peak areas or heights) of each modified peptide (typically phosphopeptide) analyte by those of the modified peptide (typically phosphopeptide) ISs.

As an alternative to using the TIQUAS technique, in the methods of the first aspect of the invention, quantification of modifications such as phosphorylation can also be carried out using MS techniques that use isotope labels for quantification, such as metabolic labeling (e.g., stable isotope labeled amino acids in culture, (SILAC); Olsen, J. V. et al. *Cell* 127, 635-648 (2006)), and chemical derivatization (e.g., iTRAQ (Ross, P. L.; et al. *Mol Cell Proteomics* 2004, 3, (12), 1154-69), ICAT (Gygi, S. P. et al. *Nat Biotechnol* 17, 994-999 (1999)), TMT (Dayon L et al, Anal Chem. 2008 Apr. 15; 80(8):2921-31) techniques. In the methods of the invention, protein modifications can be quantified with LC-MS techniques that measure the intensities of the unfragmented ions or with LC-MS/MS techniques that measure the intensities of fragment ions (such as Selected Reaction Monitoring (SRM), also named multiple reaction monitoring (MRM)).

The method of the first aspect of the invention results in a value K for a particular protein modifying enzyme in a sample. The value K for a particular protein modifying enzyme can then be compared to the value K for other protein modifying enzymes in a sample to determine which protein modifying enzyme is most active in that sample, with the higher the value K indicating the more active enzyme. The protein modifying enzymes in a particular sample can be ranked in order of their K-scores in order to do this. This allows the selection of a suitable inhibitor with which to treat a patient from whom the sample has been taken, based on the most active protein modifying enzyme in the sample, i.e. the protein modifying enzyme with the highest value K.

Accordingly, in a second aspect the present invention provides a method of identifying an inhibitor of a protein modifying enzyme with which to treat a patient, comprising:
(i) calculating the value K for each protein modifying enzyme in a sample taken from said patient using the method of the first aspect of the invention;
(ii) identifying the protein modifying enzyme with the highest value K; and (iii) selecting an inhibitor that targets the protein modifying enzyme with the highest value K.

The method of this aspect of the invention can also be used in combination with a step of treating the patient or subject with the selected inhibitor. Accordingly, in a third aspect the present invention provides a method of treating a patient in need thereof with an inhibitor of a protein modifying enzyme, comprising:
  (i) calculating the value K for each protein modifying enzyme in a sample taken from said patient using the method of the first aspect of the invention;
  (ii) identifying the protein modifying enzyme with the highest value K;
  (iii) selecting an inhibitor that targets the protein modifying enzyme with the highest value K; and
  (iv) administering said inhibitor to said patient.

The method of treatment can be of a human or an animal subject and the invention extends equally to uses in both human and/or veterinary medicine. The inhibitor is preferably administered to an individual in a "therapeutically effective amount", this being sufficient to show benefit to the individual and/or to ameliorate, eliminate or prevent one or more symptoms of a disease. As used herein, "treatment" includes any regime that can benefit a human or non-human animal, preferably a mammal, for example an economically important mammals such as cattle, sheep, goats and pigs. The treatment may be in respect of an existing condition or may be prophylactic (preventative treatment).

The patient is a patient in need of treatment with an inhibitor of a protein modifying enzyme, such as an inhibitor of a protein kinase. For example, the patient may be suffering from or suspected of suffering from cancer, such as lymphoma or leukemia, for example acute myeloid leukemia (AML). In this case, the patient is typically treated with an inhibitor of a protein kinase, typically an inhibitor of a human protein kinase selected from the group consisting of AGC kinases, for example protein kinase A (PKA), protein kinase B (PKB) (also known as Akt), protein kinase C (PKC) and protein kinase G (PKG); tyrosine kinases; tyrosine-kinase like kinases; calcium/calmodulin-dependent protein kinases; the casein kinase 1 group; CMGC group, for example CDK, MAPK, GSK3 and CLK kinases; and STE, the homologues of yeast Sterile 7, Sterile 11, and Sterile 20 kinases. Suitable kinase inhibitors for use in accordance with this aspect of the invention include AZD-5438 (CDK2i;), GF-109203X (PKCαi; Tocris), PF-3758309 (PAKi; Calbiochem), Trametinib (MEKi; Selleckchem), MK-2206 (AKTi; Selleckchem), KU-0063794 (mTORi; Chemdea), TAK 715 (P38αi;), PKC-412 (PKC/Flt3i; Tocris), TBB (CK2i;), PF-3758309 (PAKi), and C4945 (CK2i;).

Dosages of the inhibitor of a protein modifying enzyme for use in the present invention can vary between wide limits, depending upon the disease or disorder to be treated, the age and condition of the individual to be treated, etc. and a physician will ultimately determine appropriate dosages to be used.

This dosage can be repeated as often as appropriate. If side effects develop the amount and/or frequency of the dosage can be reduced, in accordance with normal clinical practice.

For administration to mammals, and particularly humans, it is expected that the daily dosage of the active agent will be from 1pg/kg to 10 mg/kg body weight, typically around 10 µg/kg to 1 mg/kg body weight. The physician in any event will determine the actual dosage which will be most suitable for an individual, which will be dependent on factors including the age, weight, sex and response of the individual. The above dosages are exemplary of the average case. There can, of course, be instances where higher or lower dosages are merited, and such are within the scope of this invention.

The present inventors have also devised a second algorithm for quantifying the activity of a protein modifying enzyme in a sample. Accordingly, in a fourth aspect the present invention provides a method of quantifying the activity of a protein modifying enzyme in a sample, comprising calculating the value SC for said protein-modifying enzyme as follows:

$$SC = -\log_2\left(\frac{P_{Ci}}{C_i} \cdot IC_{50i}\right)$$

wherein $P_{Ci}$=reduction in proliferation using inhibitor at $C_i$; $C_i$=inhibitor concentration at which proliferation is measured; and $IC_{50i}$="in vitro" $IC_{50}$ of inhibitor against primary target.

The method of the fourth aspect of the invention involves calculating the value SC based on pharmacological data obtained from in vitro experiments using inhibitors of protein modifying enzymes, such as protein kinase inhibitors. Accordingly, the "inhibitor" referred to in relation to the fourth aspect of the invention is an inhibitor of a protein modifying enzyme.

The experiments used to provide the information for calculating the value SC involve determining levels of cell proliferation in vitro in a sample before and after adding an inhibitor of a protein modifying enzyme. This allows the determination of $P_{Ci}$, which is the reduction in proliferation seen using the inhibitor at a concentration $C_i$. Proliferation can be determined using any suitable method, for example the crystal violet assay, MTS (3-(4,5-dimethylthiazol-2-yl)-5-(3-carboxymethoxyphenyl)-2-(4-sulfophenyl)-2H-tetrazolium) and Guava ViaCount.

The calculation of the value SC also involves the determination of the $IC_{50i}$, which is the in vitro $IC_{50}$ (concentration of inhibitor that reduces the activity of the protein modifying enzyme by 50% in in vitro assays) of inhibitor against its primary target, i.e. the main target of the inhibitor (since some inhibitors have effects on multiple protein modifying enzymes such as kinases). Methods for determining the $IC_{50}$ will be known to those skilled in the art. Typically, the protein modifying enzyme is a protein kinase.

The methods of the first, second and fourth aspects of the invention are typically implemented on a computer, using a computer program product. The computer program product may include computer code arranged to instruct a computer to perform the functions of one or more of the various methods described above. The computer program and/or the code for performing such methods may be provided to an apparatus, such as a computer, on a computer readable medium or computer program product. The computer readable medium may be transitory or non-transitory. The computer readable medium could be, for example, an electronic, magnetic, optical, electromagnetic, infrared, or semiconductor system, or a propagation medium for data transmission, for example for downloading the code over the Internet. Alternatively, the computer readable medium could take the form of a physical computer readable medium such as semiconductor or solid state memory, magnetic tape, a removable computer diskette, a random access memory (RAM), a read-only memory (ROM), a rigid magnetic disc, and an optical disk, such as a CD-ROM, CD-R/W or DVD.

An apparatus such as a computer may be configured in accordance with such code to perform one or more processes in accordance with the various methods discussed herein. In one arrangement the apparatus comprises a processor, memory, and a display. Typically, these are connected to a central bus structure, the display being connected via a display adapter. The system can also comprise one or more input devices (such as a mouse and/or keyboard) and/or a communications adapter for connecting the apparatus to other apparatus or networks. Such an apparatus may take the form of a data processing system. Such a data processing system may be a distributed system. For example, such a data processing system may be distributed across a network.

As described herein, the present inventors have developed two algorithms to quantify the contribution of individual protein modifying enzymes such as kinases in a given cell population to total signalling. One such algorithm, which the inventors have named Kinase Activity Ranking (KAR), produces "K-Scores" and uses quantitative MS data such as quantitative MS phosphoproteomics data as the input to generate a score that can be used to rank all protein modifying enzymes such as kinases (for which substrates are known) based on their activity. KAR may represent a generalized and principled approach to rationally select the most appropriate cell signalling inhibitor to treat individual patients. This idea is based on data, discussed in the Examples herein in more detail, that indicate that K-Scores reflect cell phenotypes (i.e., how sensitive cells are to kinase inhibitors). The second algorithm, named "Relative Sensitivity Analysis", uses pharmacological data to derive "Sensitivity Coefficients" (SCs) that can be used to compare the effects of inhibitors of protein modifying enzymes, such as kinase inhibitors, against each other within a sample. The input data for the two algorithms are obtained from protein mass spectrometry (MS) and pharmacological experiments, respectively; therefore, the two methods are orthogonal in nature.

In one embodiment, KAR uses MS-based phosphoproteomics data as the input. In this embodiment, the K-Scores generated as a result are the sum of the intensities of phosphorylated peptides known to be substrates of a given kinase divided by the sum of intensities of all phosphorylated peptides present in a sample multiplied by a correction factor that takes into account that some kinases may have a larger number of substrates than others, and that databases of kinase-substrate relationships list more substrates for better known kinases.

K-Score $$K\text{-Score} = \frac{a}{b} \times \left(\frac{m}{t}\right)^{1/2}$$

$a = \sum_{i=1}^{m} \alpha i =$ Sum of intensities of phosphorylation sites substrates of kinase $K$;

$b = \sum_{j=1}^{l} \beta j =$ Sum of all phosphorylation sites intensities $m =$ number of substrates of kinase $K$ detected $t =$ number of known subrates of kinase $K$ Accordingly, the principle of KAR (the K-score) may be illustrated as below.

K-Score (K)

$$K = \frac{\sum \alpha_i}{\sum \beta_j} \cdot \left(\frac{m}{t}\right)^{\frac{1}{2}} \cdot 10^6$$

-continued $\sum \alpha_i =$ sum of substrate intensifies for kinase $K$ $\sum \beta_j =$ sum of all phosphorylation site intensifies $m =$ number of substrates (of kinase $K$) in dataset $t =$ number of known substrates of kinase $K$ The intensities of phosphorylated peptides containing sites commonly phosphorylated by given kinases are summed and normalised to the sum of all phosphopeptide intensities. The resulting values are further normalized to the number of substrates known and identified per kinase. The intensities of phosphorylation sites can be determined by quantitative label-free MS as in the inventors' previous publications, for example the TIQUAS patent application WO 2010/119261 and the following papers:

Alcolea, M. P., Casado, P., Rodriguez-Prados, J. C., Vanhaesebroeck, B. & Cutillas, P. R. *Molecular & cellular proteomics: MCP* 11, 453-466, doi:10.1074/mcp.M112.017483 (2012).

Casado, P. et al. *Genome biology* 14, R37, doi:10.1186/gb-2013-14-4-r37 (2013).

Casado, P., Bilanges, B., Rajeeve, V., Vanhaesebroeck, B. & Cutillas, P. R. *Molecular & cellular proteomics: MCP* 13, 836-848, doi:10.1074/mcp.M113.034751 (2014).

Casado, P. & Cutillas, P. R. *Molecular & cellular proteomics: MCP* 10, M110 003079, doi:10.1074/mcp.M110.003079 (2011).

Casado, P. et al. *Science signaling* 6, rs6, doi:10.1126/scisignal.2003573 (2013).

Cutillas, P. R., Geering, B., Waterfield, M. D. & Vanhaesebroeck, B. *Molecular & cellular proteomics: MCP* 4, 1038-1051, doi: 10.1074/mcp.M500078-MCP200 (2005).

Montoya, A., Beltran, L., Casado, P., Rodriguez-Prados, J. C. & Cutillas, P. R. *Methods* 54, 370-378, doi:10.1016/j.ymeth.2011.02.004 (2011).

Rajeeve, V., Pearce, W., Cascante, M., Vanhaesebroeck, B. & Cutillas, P. R. *The Biochemical journal* 450, 619-628, doi:10.1042/BJ20121525 (2013).

Rajeeve, V., Vendrell, I., Wilkes, E., Torbett, N. & Cutillas, P. R. *Molecular & cellular proteomics: MCP* 13, 1457-1470, doi:10.1074/mcp.M113.035204 (2014).

KAR is conceptually different to the inventors' previously published algorithm, named Kinase Substrate Enrichment Analysis (KSEA), which is the subject matter of the patent application published as WO 2013/132075 and also Casado, P. et al. Science Signaling 6, rs6 (2013). The difference is that KSEA compares kinase activities across samples, whereas KAR compares the activities of different kinases against each other within a sample. Although both algorithms involve linking the intensities of phosphorylation sites to the kinases that act upstream, their outputs are in practice different because KAR can be used to rank kinase activities based on how active they are in samples, whereas KSEA cannot be used for such purpose.

While testing and developing KAR, the inventors hypothesized that the algorithm, since it is a measure of signalling strength, reflects cell phenotypes. Because there are no other methods that can be used to compare the contribution of kinases to the signalling output relative to each other, testing the accuracy of K-Scores (the ouput of KAR) as a measure of signalling strength requires assessing whether these values correlate with signalling outputs. Therefore, the inventors investigated a method, completely independent of MS-based phosphoproteomics, to quantify and rank the contribution of different kinases to signalling. Cell proliferation and viability are relevant outputs to measure because these are key endpoints of cell signalling that can be easily measured.

The outcome of this method was the "Relative Sensitivity Analysis" (RSA) algorithm, which in one embodiment derives "Sensitivity Coefficients" (SCs) for given kinases. It is based on the assumption that pharmacological inhibitors against regulatory kinases will reduce cell viability/proliferation to a greater extent than inhibitors against kinases that contribute less to signalling. This is a well-accepted concept; however, the problem of applying such an idea is that different inhibitors have different affinities against their targets, so that measuring inhibitor effects, using pharmacological concepts such as the concentration of inhibitor that reduces viability/proliferation by 50% (IC50), result in values that reflect both the affinity of inhibitors for their targets as well as the contribution of the target to the regulation of the biological process under investigation. To account for the differences in affinities, the SC expresses cell viability/proliferation as a function of concentration of inhibitor used, multiplied by the in-vitro IC50 (concentration of inhibitor that reduces of kinase activity by 50% in in vitro kinase assays) of the inhibitor against its main target. In this way, kinase inhibitors can be ranked based on the contribution that their targets have to the biological process under study (rather than by how well they inhibit their targets); thus, they can be compared to each other.

Sensitivity Coefficient, SC $$SC = -\log_2\left(\frac{P_{Ci}}{C_i} \times IC50_i\right)$$

$P_{Ci}$ = reduction in cell proliferation at $C_i$ $C_i$ = Concentration of inhibitor at which proliferation is measured $IC50_i$ = In vitro $IC50$ of inhibitor against the main target $P_{Ci}$ in the above equation may alternatively be referred to as $P_C$.

The $IC50_i$ (or $IC_{50i}$) may also be defined as as the in vitro $IC_{50}$ against the primary target.

The advantages of the methods of the present invention are as follows:

KAR provides quantification of signalling in "absolute units", i.e., analysis does not require analysis of a control sample in parallel; therefore KAR can be applied to the analysis of clinical samples.

KAR, and associated K-scores is a predictive measure of how sensitive cells are going to be to inhibitors of cell signalling, which makes it useful in the development of personalized medicines.

All kinase activities and signalling pathways are measured in a single assay that can be performed in a clinically useful timeframe. This is in contrast to most immunochemical techniques which measure a single pathway per assay.

The methods do not depend on the availability of antibodies with sufficient specificity.

RSA allows testing the contribution of inhibitor targets to the regulation of cell proliferation/viability.

Preferred features for the second and subsequent aspects of the invention are as for the first aspect mutatis mutandis. It will be appreciated that all embodiments described herein are considered to be broadly applicable and combinable with any and all other consistent embodiments, as appropriate. Such combinations are considered to fall within the scope of the present invention.

The present invention will now be further described by way of reference to the following Examples which are present for the purposes of illustration only. In the Examples, reference is made to a number of Figures in which:

FIG. 1. Reproducibility, linearity and accuracy of K-score determination._(a) The principle of Kinase Activity Ranking (KAR, which produces K-scores). The intensities of phosphorylated peptides containing sites commonly phosphorylated by given kinases are summed and normalised to the sum of all phosphopeptide intensities. The resulting values are further normalized to the number of substrates known and identified per kinase. (b) Experimental design to assess quantitative nature of the algorithm. (c, d), Reproducibility, and linearity of K-scores for three representative kinases. (e) Ranking of kinases based on K-scores as a function of pV treated cells. Tyrosine kinases (shown as triangle data points) clearly increase their K-score-based ranks as a function of pV treated extracts present in samples.

Figure 2:
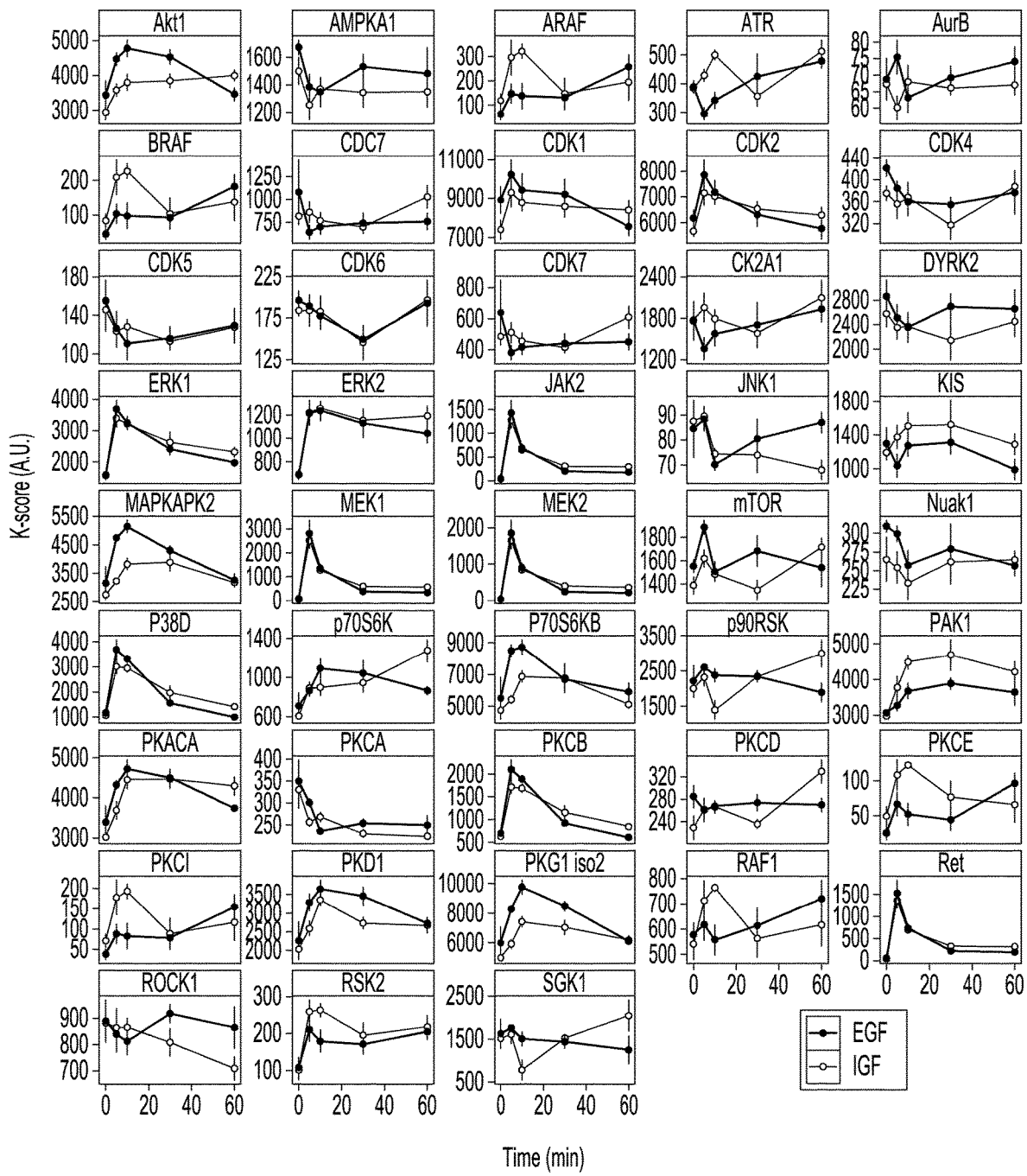

FIG. 2. K-scores as a function of EGF or IGF treatment. The phosphoproteomics data in Wilkes et al PNAS 112, 7719-7724 (2015) was processed for KAR analysis. The results illustrate that the outputs of KAR (K-scores) are a measure of kinase activity as these values show the expected kinetics of growth factor stimulation on kinase activity.

Figure 3:
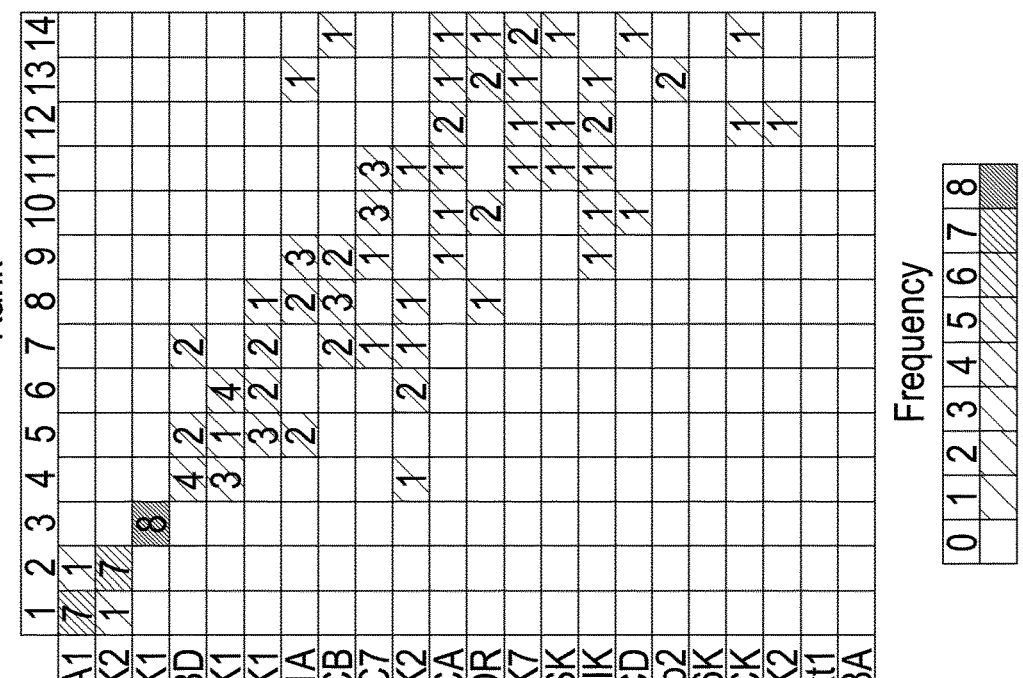
Figure 3:
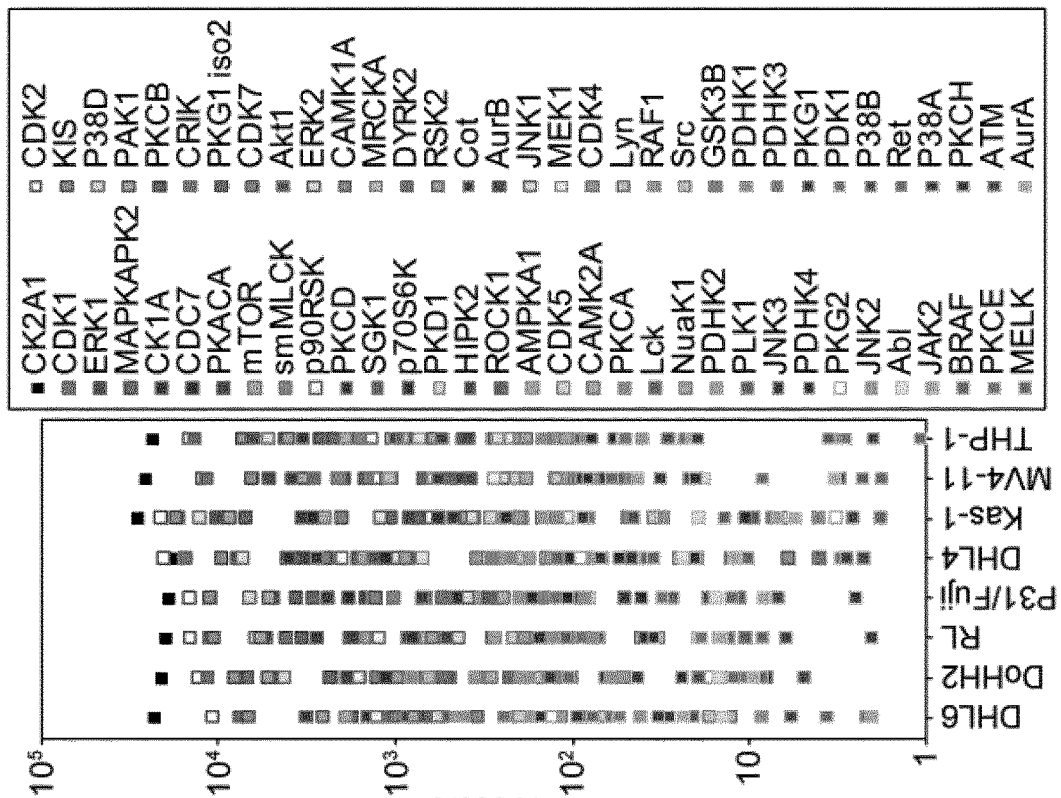

FIG. 3. The K-score ranks kinase activities based on their contribution to cellular phosphorylation relative to each other. (a) K-scores of over 60 kinases across eight haematological cell-lines. Phosphoproteomics experiments were performed on the named cell-lines in four independent occasions as previously described and each was analysed twice by LC-MS/MS. Mean K-scores of the eight analytical replicates are shown. (b) Ranking of kinases based on their contribution to total cellular phosphorylation as determined by KAR analysis.

Figure 4:
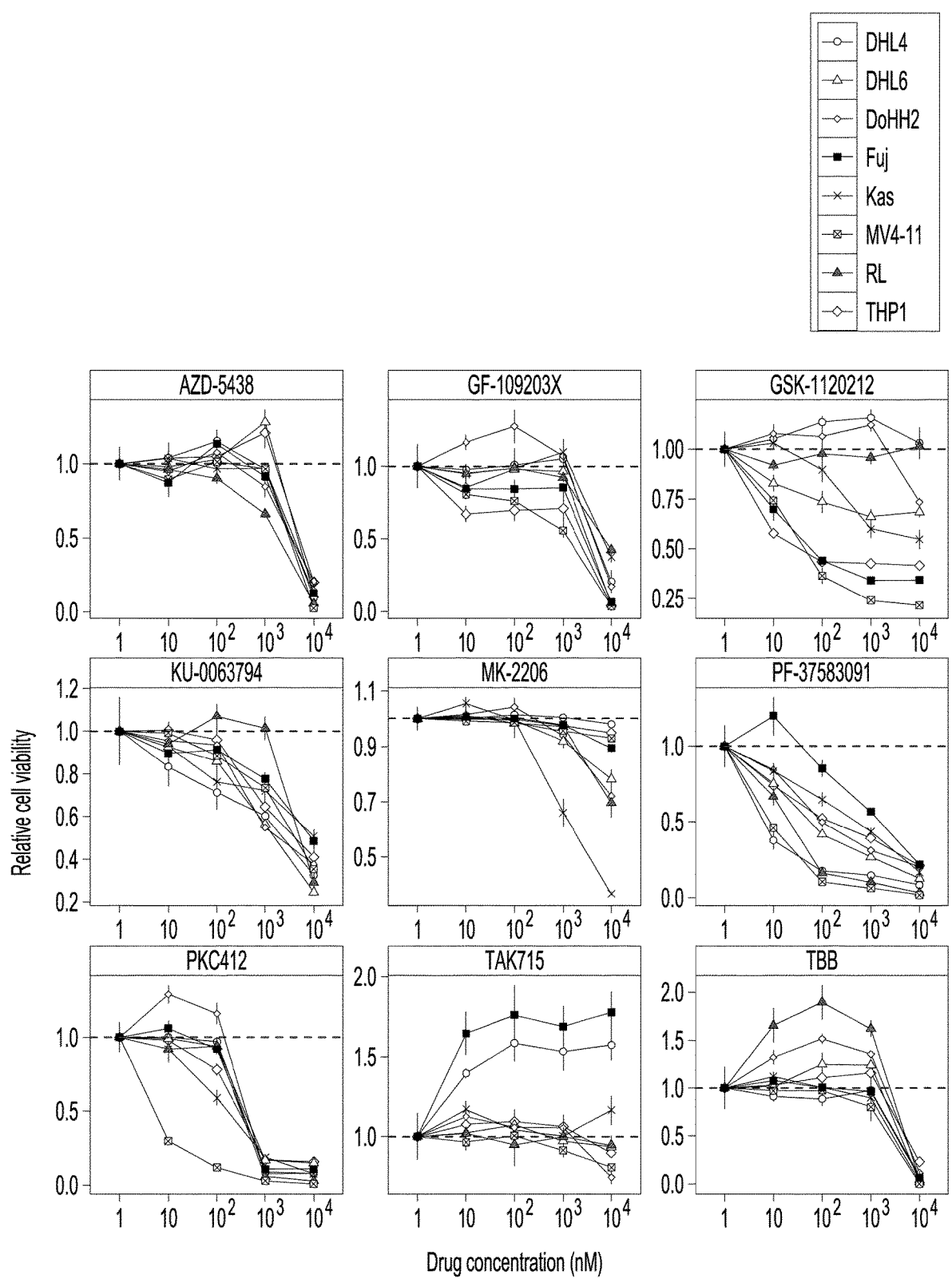

FIG. 4. Dose response curves of hematological cell lines treated with a panel of kinase inhibitors. The named cell lines were treated with the inhibitors shown and viability measured using a Guava assay after 72 h of treatment. Data points are mean±SD (n=4).

Figure 5:
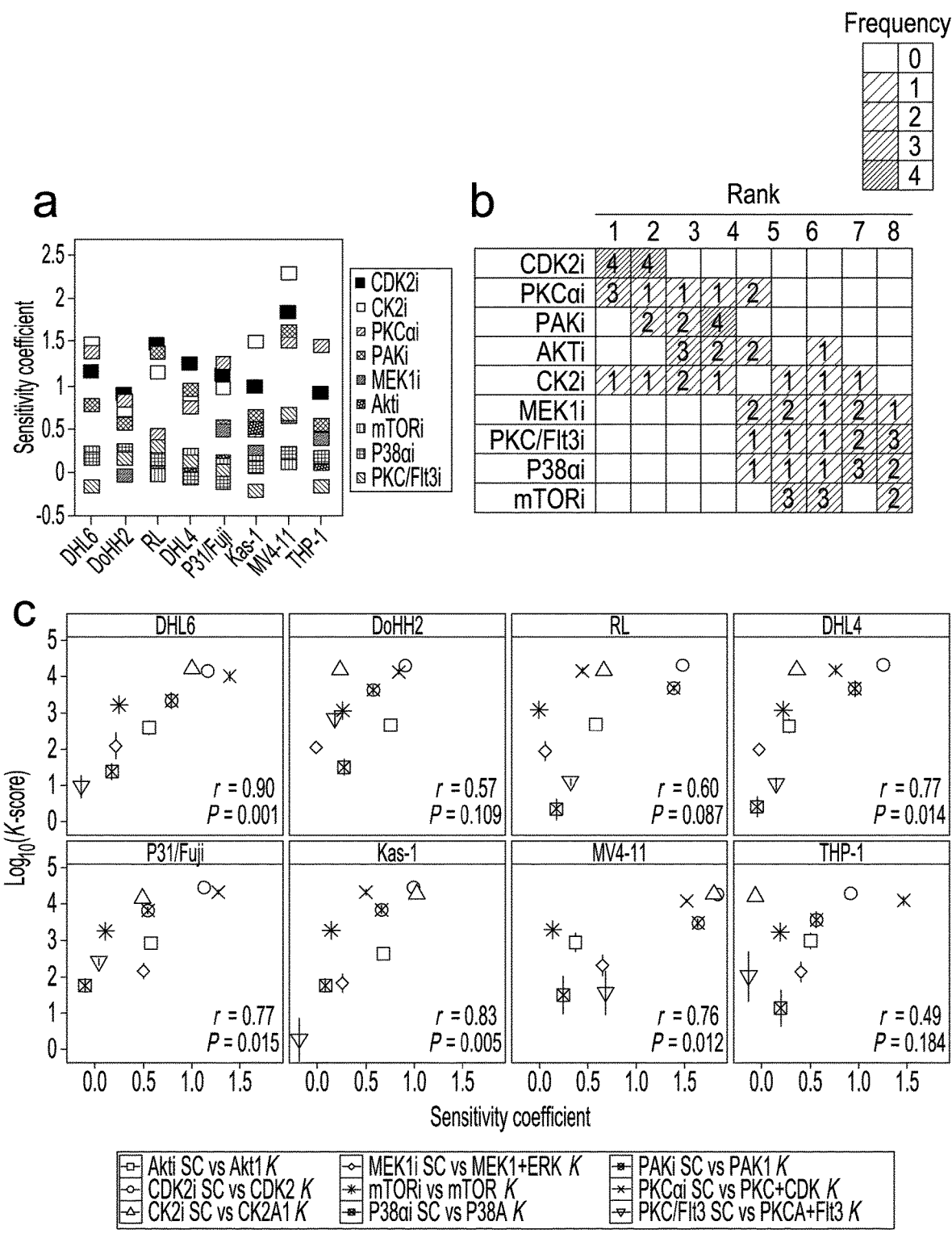

FIG. 5. Kinase activity Ranking models the contribution of kinase activities to cell viability in haematological cell-lines. (a) SC (sensitivity coefficient) of the named compounds across eight haematological cell-lines. (b) Frequency of ranks of kinase inhibitors based on their SC across cell-lines. (c) Association between kinase activity (as measured by KAR, FIG. 1) and SC within individual cell-lines. K-score values are shown as mean±SEM of four independent experiments, each measured in duplicate. r, pearson correlation coefficient; p values were derived from r values.

Figure 6:
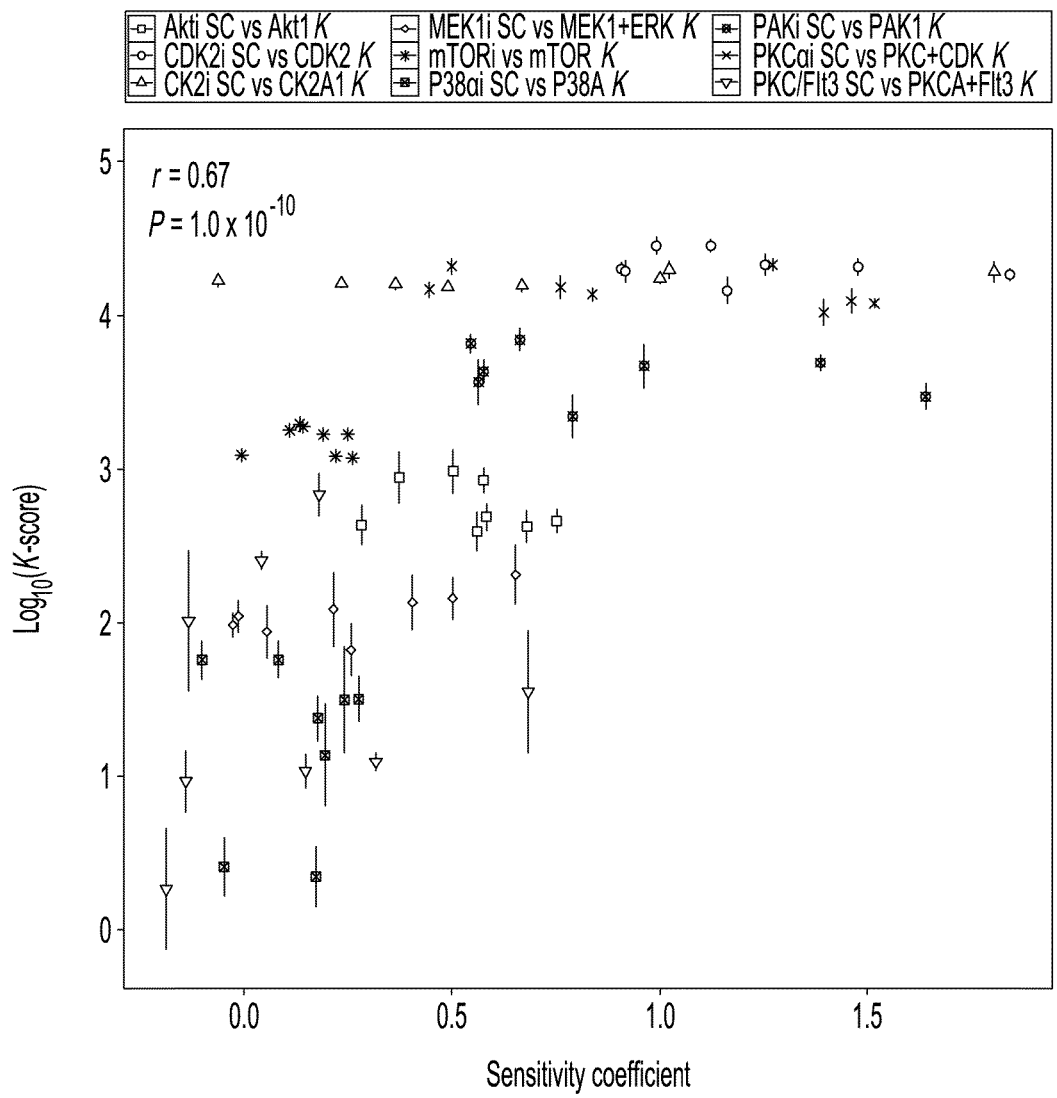

FIG. 6. Relationship between K-scores and sensitivity to kinase inhibitors across eight hematological cell lines. Linear regression analysis measured across 8 cell lines shows that Sensitivity Coefficient for 9 different drugs were significantly associated with the K-scores for their main target kinases.

Figure 7:
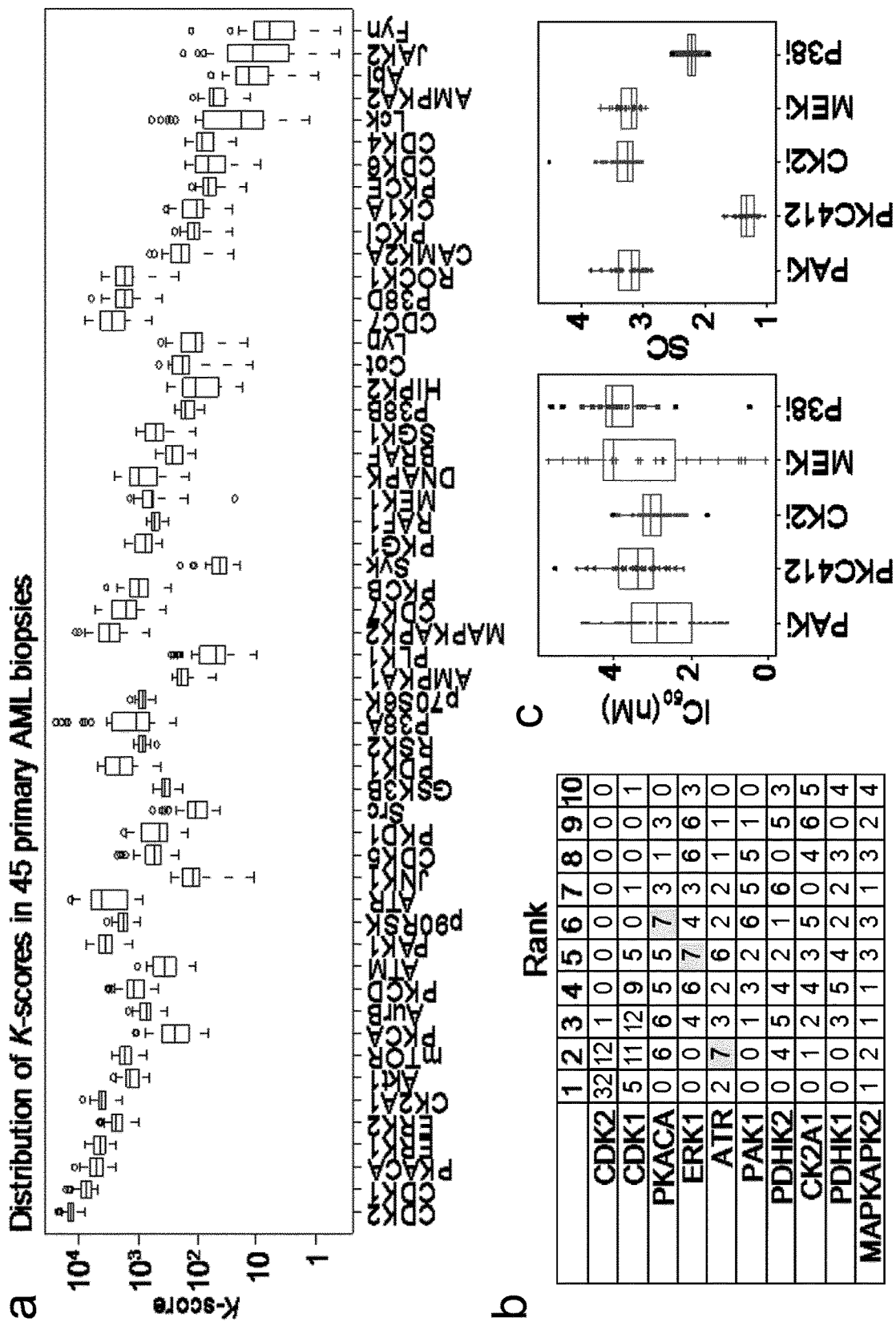
Figure 7:
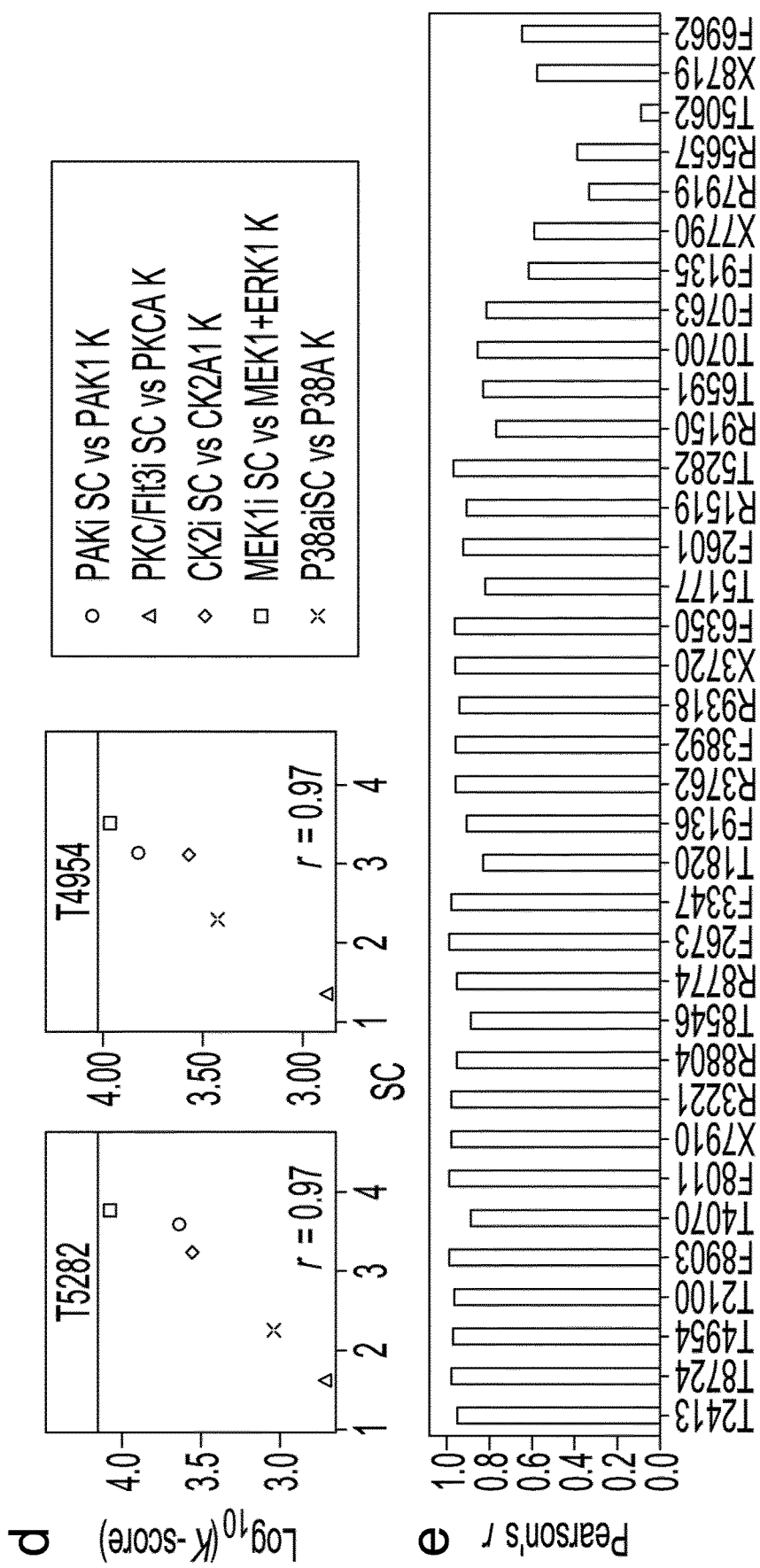
Figure 7:
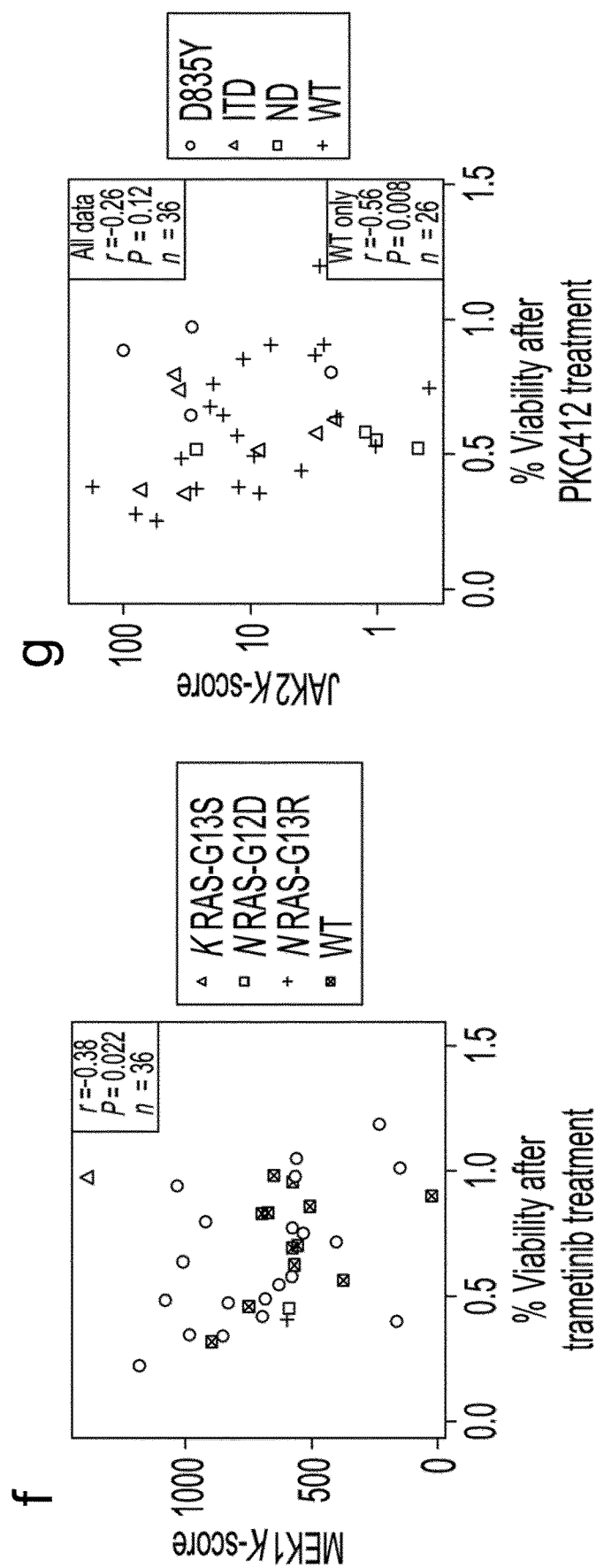

FIG. 7. Modelling the contribuon of kinase activity to acute myeloid leukemia (AML) cell viability. (a) Distribution of K-scores in 45 primary AML biopsies. (b) Frequency of ranks of the named kinases as determined by K-score analysis. (c) Distribution of $IC_{50}$s and SCs in 36 AML biopsies treated with the named kinase inhibitors; P38i, TAK775; CK2i, CX494; MEKi tramentinib (inhibits MAPK signalling); PAKi, PF-03758309. (d) Association between SC and K-scores in two representative AML patient samples and in 36 cases of primary AML (e). (f,g) Correlation between K-scores for MEK1 and JAK2 and cell viability as a function of MEKi and PKC412 treatment, respectively.

Figure 8:
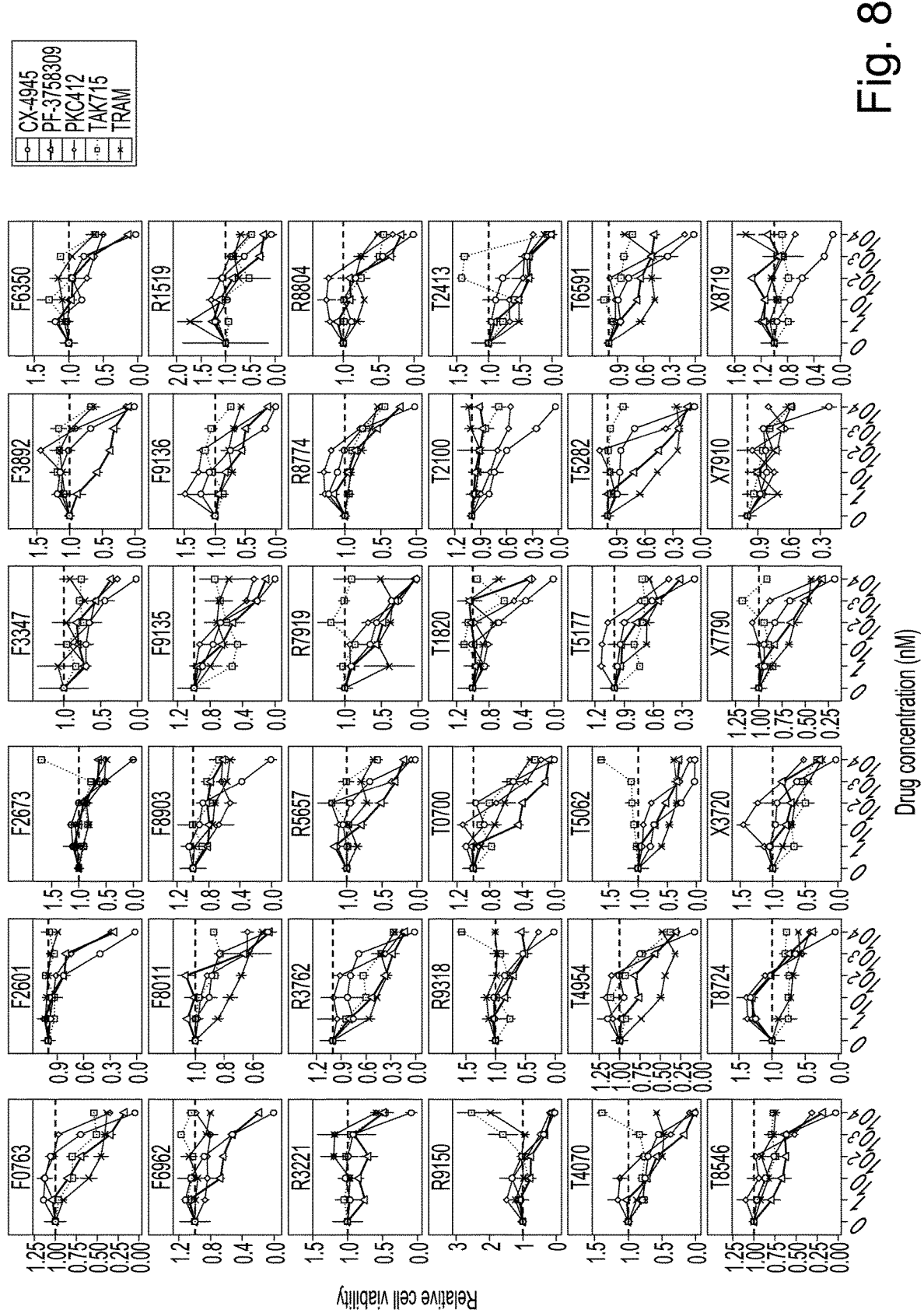

FIG. 8. Dose response curves of primary AML cells treated with a panel of kinase inhibitors. AML biopsies were obtained from the Barts Cancer Institute biobank with ethical consent, treated with the named compounds for 72 h and viability measures using Guava ViaCount assay. Data points are mean±SD (n=3).

Figure 9:
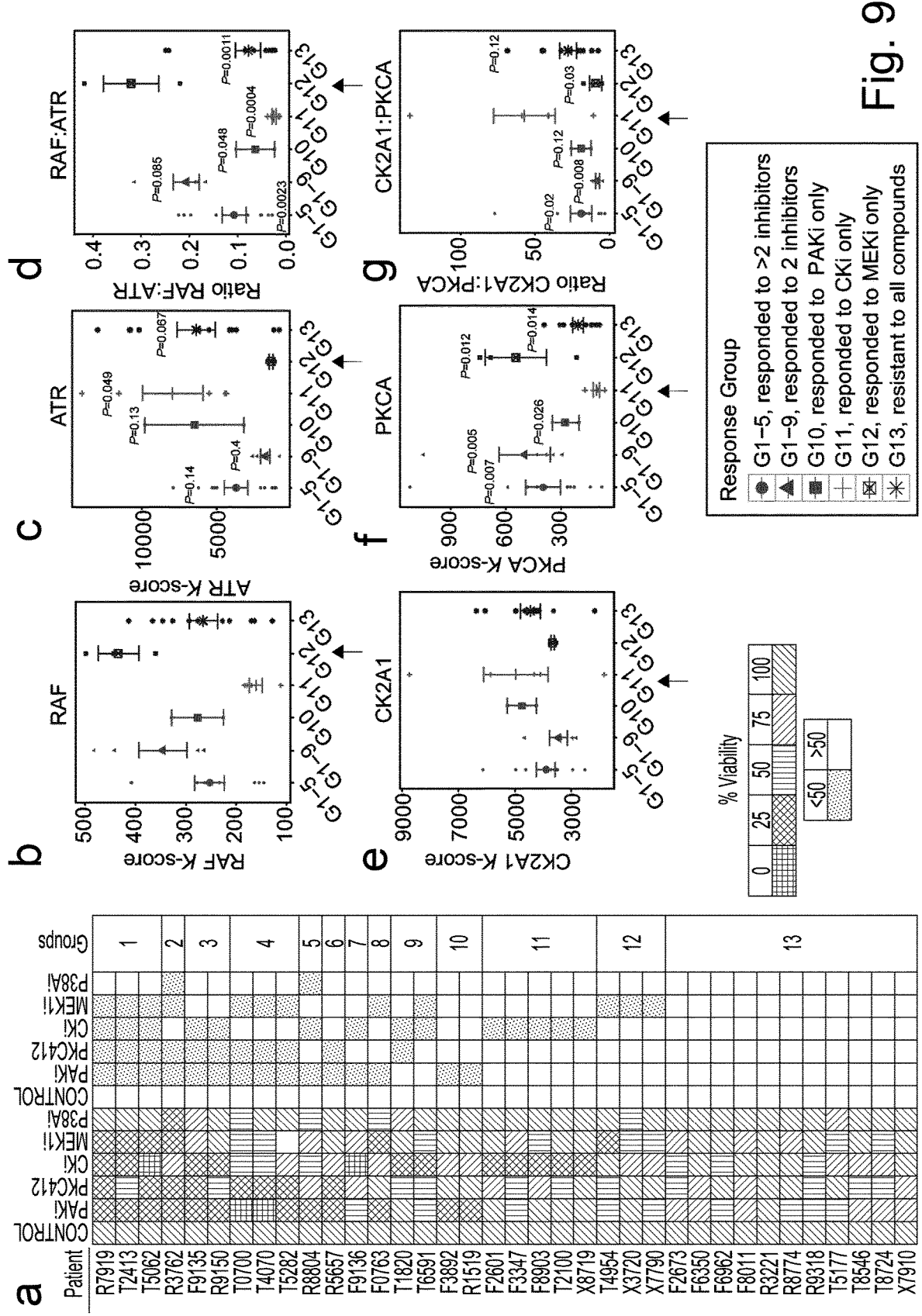

FIG. 9. Complex drug response phenotypes are associated with differences in kinase activities. (a) Patterns of responses to five kinase inhibitors in primary AML cells. Sensitivity was measured at five inhibitor concentratons. The heatmap shows viability at 1 µM concentration (left) and a decrease in viability by >%50 is denoted by green boxes (right). A total of 13 groups based on responses were identified which could be further classified into five main response groups. (b-g) K-scores for the named kinases, or their ratios, across the response groups. Individual K-scores were normalised to the average across patients. Shown are the mean±SEM and individual values within response groups. P-values were calculated through an unpaired t-test against the responses groups 12 or 11 in (c), (d) and (f), and (g) respectively.

Figure 10:
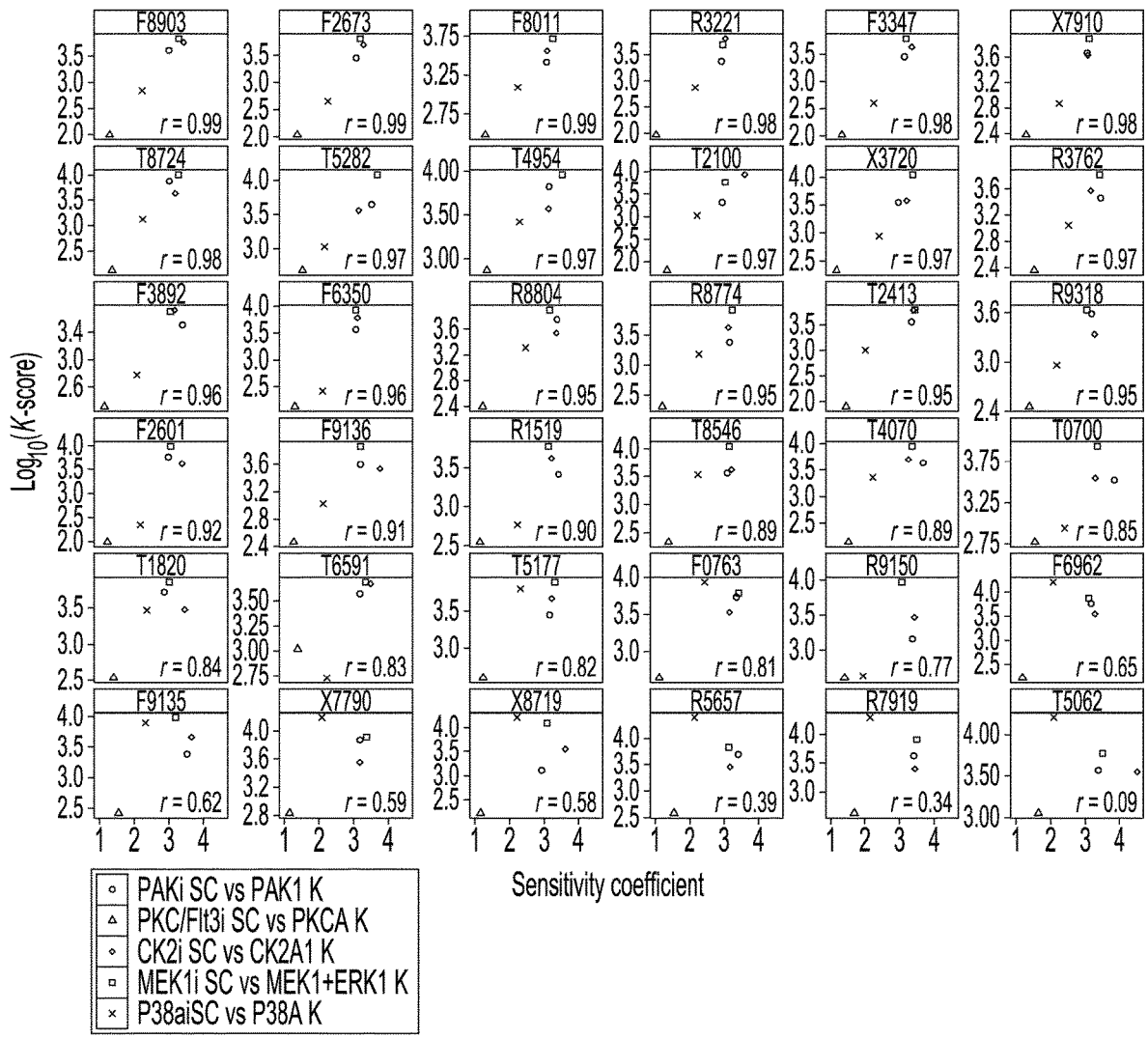

FIG. 10. Models of cell viability in a panel of primary AML biopsies. K-Scores and Sensitivity Confidents were obtained from phosphoproteomics and cell viability data, respectively, and compared in 36 different AML patient biopsies.

Figure 11:
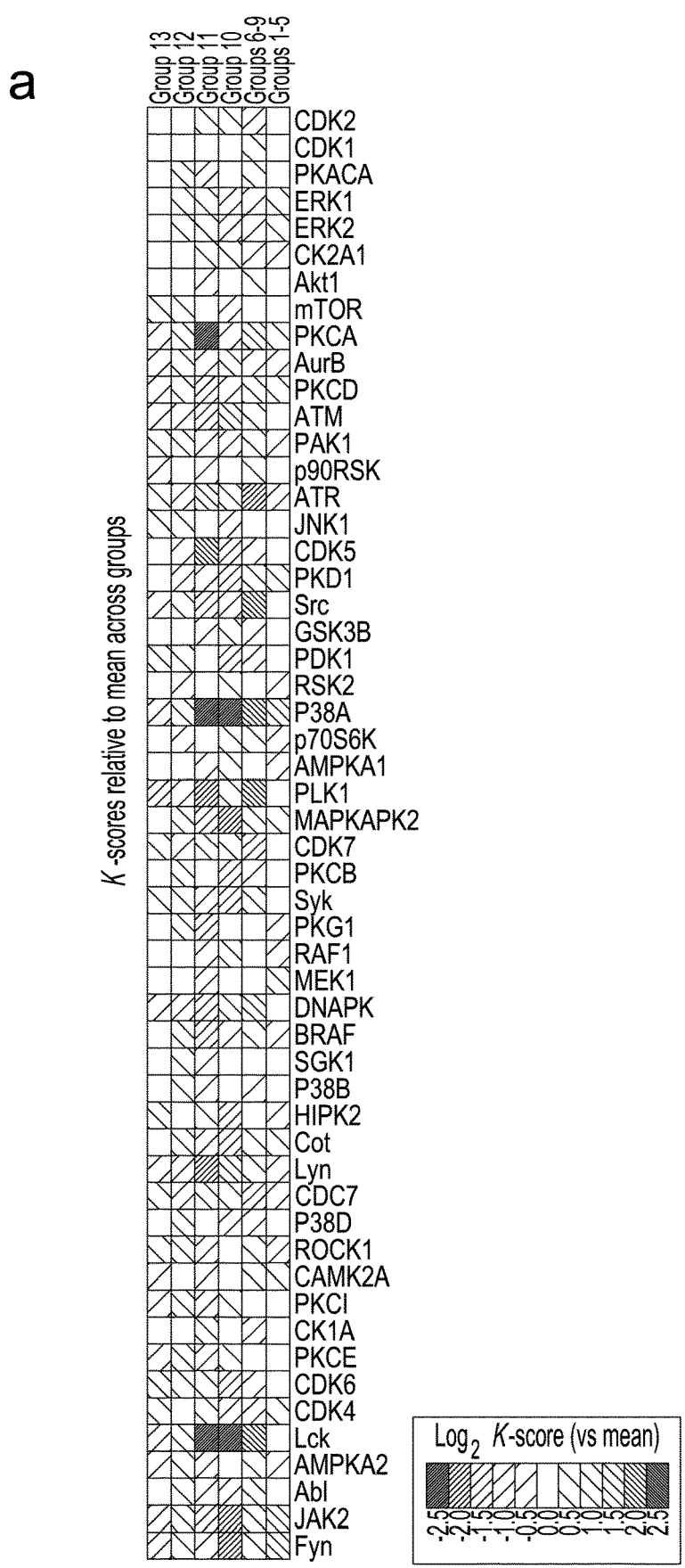
Figure 11:
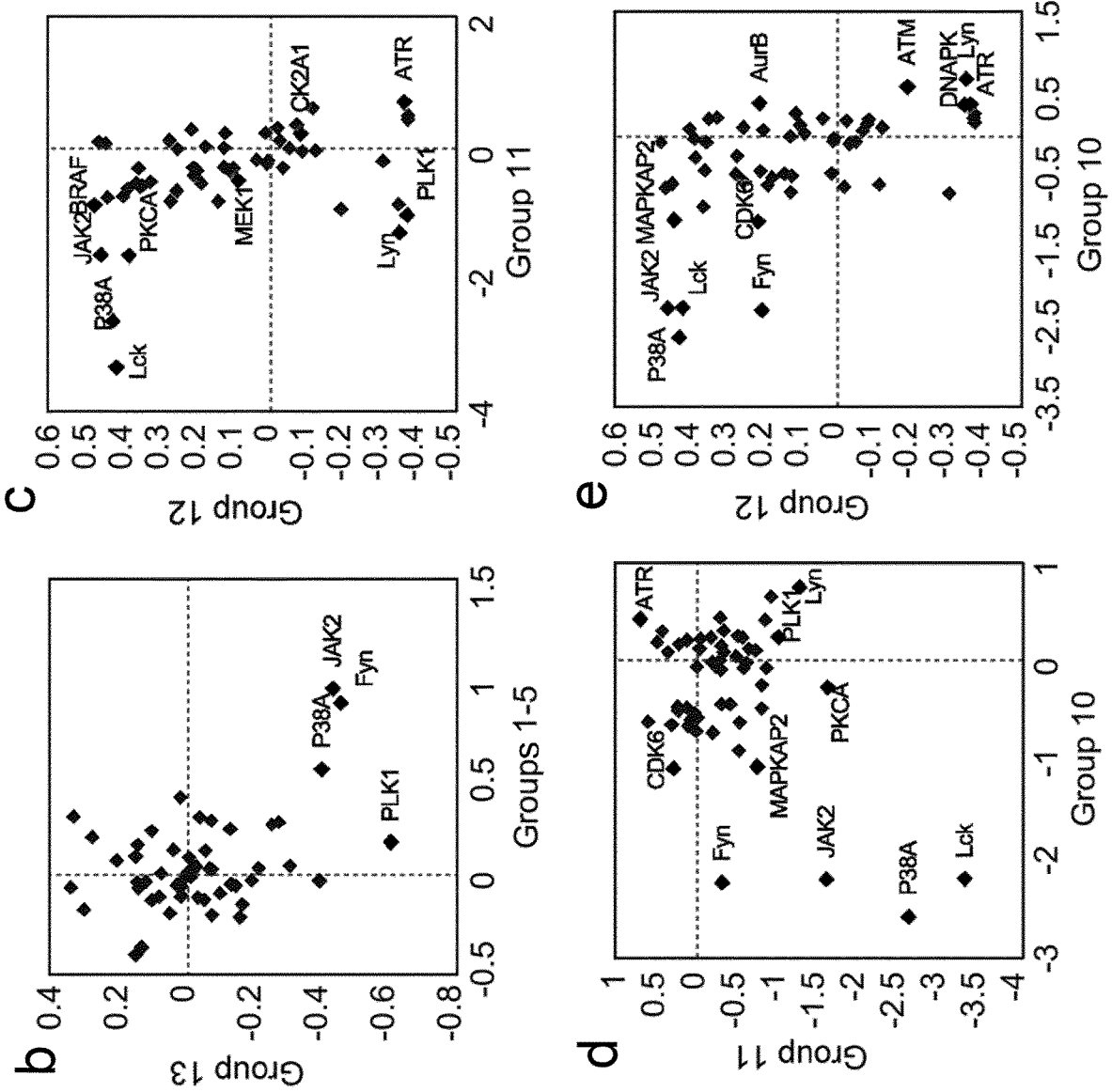

FIG. 11. Kinase activities associated with patterns of responses to kinase inhibitors. (a) K-scores were normalized to the average across the response groups shown in FIG. 4a of the main text (average of the row) and log transformed. (b) Comparison of K-scores between cells sensitive to at least 3 compounds (Groups 1-5) with those from cells resistant to all compounds (Group 13) showing kinase activities increased in sensitive cells (red fonts). (c) Comparison of K-scores between cells sensitive to MEK1i only (group 12) and those sensitive to CK2i only (Group 11). (d) Comparison of K-scores between cells sensitive to CK2i only (group 11) and those sensitive to PAKi only (Group 10). (e) Comparison of K-scores between cells sensitive to MEK1i only (group 12) and those sensitive to PAKi only (Group 10).

EXAMPLE

Materials and Methods

Cell Culture

B-cell lymphoma and leukemia cell-lines were routinely maintained in RPMI-1640 medium supplemented with 10% fetal-bovine serum (FBS) and 100 U·mL$^{-1}$ penicillin/streptomycin (P/S). Cells were maintained at a confluency of 0.5-2.0×10$^6$ cells·mL$^{-1}$. Stromal cells were grown in IMDM medium (supplemented with 10% FBS and 100 U·mL$^{-1}$ P/S) and maintained at a confluency of 2.0-30.0×10$^6$ cells in 175 cm$^2$ flasks. MS-5 conditioned IMDM medium was generated by growing stromal cells in IMDM for 3 days. All cells were kept at 37° C. in a humidified atmosphere at 5% CO$_2$.

Primary AML Cells

All patients gave informed consent for the storage of their blood cells for research purposes. Each procedure was conducted in accordance with the East London and City Research Ethics Committee, as previously described (Miraki-Moud, F. et al. *Blood* 125, 4060-4068 (2015)). All studies comply with the rules of the Review Board and by the revised Helsinki protocol. Peripheral blood was extracted from AML patients at St Bartholomew's Hospital and mononuclear cells, isolated using Ficoll gradient followed by red cell lysis, were stored in liquid N$_2$. Primary AML blasts were thawed following standard procedures: briefly, vials were defrosted at 37 C and exposed to 500 µg of DNAse (Sigma) for 5 minutes. 10 mL of PBS, supplemented with 2% FBS, was added and cell suspension was centrifuged at 1500 rpm for 5 min at 5° C. Cells were resuspended in MS-5 conditioned IMDM medium and filtered using a 70 µm strainer (Fisherbrand). Cell number and viability were determined by trypan blue staining using a Vi-CELL XR cell viability analyser (Beckman Coulter).

Cell Lysis and Protein Digestion

For each cell-line, 4 independent biological replicates were performed: 10×10$^6$ cells were seeded at 0.5×10$^6$ cells·mL$^{-1}$ and left overnight. For each AML primary sample, 10×10$^6$ cells were seeded at 1×10$^6$ cells·mL$^{-1}$ and left in the incubator for 2 h. Cells were subsequently harvested by centrifugation, washed twice with ice-cold phosphate-buffered saline—supplemented with 1 mM Na$_3$VO$_4$ and 1 mM NaF—and lysed in 0.2 mL of ice-cold urea lysis buffer (8M urea in 20 mM HEPES (pH 8.0), supplemented with 1 mM Na$_3$VO$_4$, 1 mM NaF, 1 mM Na$_2$H$_2$P$_2$O$_7$ and 1 mM β-glycerol phosphate). Lysates were further homogenized by sonication and any insoluble material removed by centrifugation. Protein concentration was estimated via the bicinchoninic acid (BCA) assay. After normalizing each condition to a common protein concentration (0.5 µg·µL$^{-1}$), each sample was reduced and alkylated by sequential incubation with 10 mM dithiothreitol and 16.6 mM iodoacetamide for 30 min at room temperature, in the dark. For protein digestion, the urea concentration was reduced to 2M through the addition of 20 mM HEPES (pH 8.0). Immobilized tosyl-lysine chloromethyl ketone (TLCK)-trypsin was then added, and samples incubated overnight at 37 C. Trypsin beads were removed by centrifugation and the resultant peptide solutions were desalted using OASIS HLB 1 cc solid phase extraction cartridges as described previously (Montoya, A. et al. *Methods* 54, 370-378 (2011)).

Phosphopeptide Enrichment

Phosphorylated peptides were enriched using TiO$_2$(GL Sciences) as previously described (Wilkes, E. H. et al. *Proceedings of the National Academy of Sciences of the United States of America* 112, 7719-7724 (2015)). The resulting phosphopeptide solutions were snap-frozen, dried with a SpeedVac, and stored at −80° C. until further use.

LC-MS/MS Phosphoproteomics Analysis

For cell-line samples, each biological replicate was analyzed twice by LC-MS/MS as follows: phosphopeptide pellets were re-suspended in 14 µL of 0.1% TFA and 4.0 µL per technical replicate was injected into a Waters NanoACQUITY UPLC system (Waters, Manchester, UK) coupled online to an LTQ-Orbitrap-XL mass spectrometer (Thermo Fisher Scientific). The samples were separated on a 100 minute linear gradient between 5 and 35% ACN on an ACQUITY BEH130 C$_{18}$ UPLC column (15 cm×75 µm, 1.7 µm, 130 Å) at a flow rate of 300 nL·min$^{-1}$. The top five most intense multiply charged ions in each MS$^1$ scan were selected for collision-induced dissociation fragmentation (with multistage activation enabled). The resolution of the MS$^1$ was set to 30,000 FWHM.

For the primary AML samples, each technical replicate (two per sample) consisted of a 3.0 µL injection into a Dionex Ultimate nRSLC system (Thermo Fisher Scientific) coupled online to a Q-Exactive Plus (QEP) mass spectrometer (Thermo Fisher Scientific). The samples were separated on a 120 min linear gradient between 3 and 30% ACN on an Acclaim PepMap $C_{18}$ RSLC column (25 cm×75 µm, 2 µm, 100 Å) at a flow rate of 300 nL·min$^{-1}$. The top twenty most intense multiply charged ions present in each MS$^1$ scan were selected for higher-energy collision-induced dissociation (HCD). The resolution of the MS$^1$ scans was set to 70,000 FWHM.

Phosphopeptide Identification and Quantification

Peptide identification was performed by matching deisotoped, MS/MS data to the Uniprot Swissprot human protein databases (September 2014 release, containing 20,233 entries), utilizing the Mascot server version 2.4. Mascot Distiller was used to generate peak lists in the mascot generic format. Mass tolerances were set to 10 ppm and 600 mmu (XL)/25 mmu (QEP) for the precursor and fragment ions respectively. For the phosphoproteomics experiments, the allowed variable modifications were: phospho-Ser, phospho-Thr, phospho-Tyr, pyro-Glu (N-terminal), and oxidation-Met. The identified phosphopeptides from each of the samples were collated and curated using in-house scripts. Unique phosphopeptides ions with expectancy <0.05 were then included in the subsequent analyses. Mascot decoy database searches showed that with these settings produce a false discovery rate of ~1%. Peptide quantification was performed as described before by our group (Montoya et al. (2011), supra; Casado, P. & Cutillas, P. R. *Molecular & Cellular Proteomics*: MCP 10, M110 003079 (2011); Cutillas, P. R. & Vanhaesebroeck, B. *Molecular & Cellular Proteomics* 6, 1560-1573 (2007)) and others (Tsou, C. C. et al. *Molecular & Cellular Proteomics: MCP* 9, 131-144 (2010); Mann, B. et al. Rapid Communications in *Mass Spectrometry: RCM* 22, 3823-3834 (2008)). Briefly, Pescal software (written in Python v2.7) was then used to obtain peak areas of extracted ion chromatograms of each of the phosphopeptide ions in the database, across all of the samples being compared. The retention times of each phosphopeptide ion, in each sample, were predicted through alignment of common phosphopeptides' retention times using an in-house linear modelling algorithm. Chromatographic peaks obtained from extracted ion chromatograms for each phosphopeptide in each sample were then integrated and the peak areas recorded. The mass-to-charge (m/z) and retention time ($t_R$) tolerances were set to 7 ppm and 1.5 min, respectively.

Kinase-Substrate Enrichment Analysis and Kinase Activity Ranking

Technical replicates were averaged and peak areas for each phosphopeptide ion were then normalized to the sum of peptide intensities for each sample. Kinase-substrate matching was performed on these data as reported before (Casado, P. et al. *Science Signaling* 6, rs6 (2013)) using a VBA script against the PhosphoSitePlus database (downloaded in July 2014). Kinase Activity Ranking (KAR) was calculated for kinase K using the equation below (where m=the number of phosphorylation sites in the dataset matched to kinase K; α=the normalized intensity of the phosphorylation site i; l=the total number of phosphorylation sites in the dataset regardless of any kinase-substrate association; β=the normalized intensity of the phosphorylation site j; t=the total number of known target phosphorylation sites in the PhosphoSitePlus database for kinase K). Data were visualized either using Microsoft Excel 2007/2010 or within the R statistical computing environment (v3.0.0) using a combination of the reshape2 and ggplot2 packages.

$$K = \frac{\sum_{i=1}^{m} \alpha_i}{\sum_{j=1}^{l} \beta_j} \cdot \left(\frac{m}{t}\right)^{1/2} \cdot 10^6$$

Pervanadate Treatment

P31/Fuj cells were exposed to 1 mM sodium pervanadate or left untreated during 30 min (Sodium pervanadate was prepared by mixing 30% $H_2O_2$ and 100 mM $Na_3VO_4$ pH 8.0 at 1:100 ratio during 15 min). Cells were then harvested and lysed as outlined above. After homogenization and protein quantification, treated and untreated cell lysates were mixed to a final protein concentration of 1.0 µg·µL$^{-1}$. The proportions used were 0%, 25%, 50%, 75% and 100% of pervanadate treated extracts with 100%, 75%, 50%, 25% and 0% of untreated extracts. Protein mixtures were subsequently subjected to trypsin digestion and phosphopeptide enrichment as described above.

EGF and IGF Treatment

KAR results were obtained from a meta-analysis of Supplementary Dataset 2 in Wilkes et al. (2015), supra. Briefly, MCF-7 cells were starved for 24 h, and subsequently treated with 100 ng-mL$^{-1}$ EGF or IGF-1 for 0, 5, 10, 30 or 60 min and processed for MS analysis as described in Wilkes et al. (2015), supra. K-scores were calculated as described above.

Viability Analysis and Sensitivity Coefficient

Cell-lines were seeded in 96 well plates (10,000 cells-well-), left overnight and treated with vehicle, or 1 to 1000 nM of AZD-5438 (CDK2i;), GF-109203X (PKCαi; Tocris), PF-3758309 (PAKi; Calbiochem), Trametinib (MEKi; Selleckchem), MK-2206 (AKTi; Selleckchem), KU-0063794 (mTORi; Chemdea) or TAK 715 (P38αi;). Cells were also treated with 0.01 to 10 µM of PKC-412 (PKC/Flt3i; Tocris) or 0.1 to 10 µM of TBB (CK2i; Sigma). After 72 h, cells were stained with Guava ViaCount reagent (Millipore) as indicated by the manufacturer and cell number and viability was measured using a Guava EasyCyte Plus instrument. AML primary cells were thawed as described above, resuspended in MS-5 conditioned IMDM medium, seeded in 96 well plates (20,000 cells-well-1) and treated with vehicle or 1 to 10000 nM of PF-3758309 (PAKi), PKC412 (Flt3/PKCi), CX4945 (CK2i; Selleckchem), Trametinib (MEKi) and TAK 715 (P38i). After 72 h, cells were stained with Guava ViaCount reagent and cell number and viability was measured. All drugs were solubilized in DMSO and all measurements were performed in triplicate. Flow cytometry data were analyzed using CytoSoft (v2.5.7). IC$_{50}$ values were calculated using Graphpad PRISM (v5.03). The sensitivity coefficient (SC) was calculated using the equation below (where $P_{Ci}$=reduction in proliferation at $C_i$, IC$_{50}$="in vitro" IC$_{50}$ against primary target, and $C_i$=inhibitor concentration at which proliferation is measured). Data were visualized using Microsoft Excel 2007/2010 or within the R statistical computing environment (v3.0.0), using a combination of the reshape2 and ggplot2 packages.

$$SC = -\log_2\left(\frac{P_{Ci}}{C_i} \cdot IC_{50i}\right)$$

Results

Linearity and Reproducibility of Signaling Quantification Using Kinase Activity Ranking We first investigated the reproducibility and quantitative nature of Kinase Activity Ranking (KAR, which produces K-scores) as a measure of net kinase activity. To this end, the DHL6 cell line was treated with sodium pervanadate (pV) and after lysis mixed with lysates from untreated cells at different proportions (FIG. 1b). To test the reproducibility of the analysis, we performed this experiment on three independent occasions and each was analyzed in analytical triplicate. As expected, pV, a tyrosine phosphatase inhibitor, induced an increase in the K-Score of tyrosine kinases; which consequently ranked higher in samples as a function of pV-treated cells (FIG. 1c-e). Thus these data show that K-scores are quantitative readouts of kinase-substrate groups and suggest that these values may be used to rank kinases based on their activation status in a reproducible manner. We also performed a meta-analysis of published phosphoproteomics data obtained from time-course experiments of cells treated with EGF or IGF (Wilkes et al. (2015), supra). We observed that K-scores for serine/threonine and tyrosine kinases changed upon treatment with these growth factors with the expected kinetics (FIG. 2) indicating that KAR outputs (K-scores) truly reflect the expected kinase activities.

Kinase Activity Ranking (KAR) Models the Contribution of Kinase Activities to Cell Viability in Haematological Cell-Lines We then analyzed eight hematological cancer cell-lines and ranked >100 kinases based on their activation relative to each other. FIG. 3a shows the 60 kinases with greater K-scores, with CDK1, CDK2, ERK1, PAK1 and CK2 ranking the highest (FIG. 3b).

To investigate whether the K-scores reflected the contribution of kinases to cell viability, we reasoned that if kinases with high K-scores were contributing more to cell survival than those with lower K-scores, a correlation should exist between the K-scores of individual kinases and the impact of their inhibition on cell viability. We therefore measured cell viability of our eight cell-line panel as a function of treatment with nine kinase inhibitors (dose-response curves are shown in FIG. 4). In order to titrate enzyme inhibition in an acute manner, we opted to use pharmacological inhibitors (as opposed to genetic means). However, the effect of small molecule inhibitors on cell behavior is dependent on both the contribution of the target to the pathway flux as well as the affinity of the compound to the target (which is reflected by the in vitro $IC_{50}$). To account for this, we normalized the drug-induced inhibition of cell viability by the reported in vitro $IC_{50}$ of the compound against its known targets. We termed this value the "Sensitivity Coefficient" (SC), which was calculated as defined herein. By doing this, differences in inhibitor potencies were normalized, and kinase inhibitors with disparate in vitro $IC_{50}$ values could be ranked against each other based on the contribution of their targets to cell viability.

TABLE 1

A panel of haematological cell-lines were treated with the named compounds and their viability measured after 48 hours using the Guava Viacount assay.

| Ref | Name | Targets |
|---|---|---|
| CDK2i | AZD5438 | CDK1, CDK2, CDK9, GSK3B |
| PKCαi | GF109203X | PKCA, CDK2 |
| MEK1i | GSK1120212 | MEK1 |
| mTORCi | KU-0063794 | mTORCi, mTORC2 |
| PAKi | PF03758309 | PAK1, PAK4, AMPK |
| PKC/Flt3 | PKC412 | PKCs, Flt3, Kit |
| P38αi | TAK715 | P38A |
| CK2i | TBB | CK2A1 |
| Akti | MK2206 | Akt1, Akt2 |

Ranking the kinase inhibitors shown in Table 1 based on their SCs demonstrated that CDK2i and PAKi were ranked the highest, and overall, the ranking frequencies mirrored those obtained through KAR (FIG. 5a,b). It should be noted that the PKCα inhibitor (PKCαi) also inhibits CDK2 with high potency. A more direct comparison revealed a strong association between K-scores of specific kinases with the SCs against their inhibitor (FIG. 5c). Overall, KAR accurately modeled viability in the eight cell-lines tested, as assessed by linear regression analysis (Pearson r values ranging from 0.49 to 0.90 with a mean of 0.76, P=0.016), and overall, the model showed a statistically significant relationship between the two metrics (r=0.67; P=1.0×10$^{-10}$; 4 FIG. 6). These data show that KAR accurately modeled the contribution of kinases to cell viability in in vitro cell-line cultures.

Kinases Activity Ranking (KAR) Models the Contribution of Kinase Activities to Cell Viability in AML Primary Cells.

To determine whether the approach may be able to identify regulatory kinases in an independent set of cells, we measured the phosphoproteomes of 45 primary AML biopsies, enriched with cases of normal karyotype, an intermediate risk marker for the disease. KAR of the resulting dataset (FIG. 7a) indicated that, as with the experiments in cell-lines, CDKs, ERK1, CK2A1 and PAK1 were frequently ranked highly in these primary cancer cells (FIG. 7b). In contrast with the cell-lines, however, ATR and PKACA also ranked highly in a number of patients.

To investigate whether KAR reflected the contribution of their respective kinases to viability in primary AML samples, the cells were treated with inhibitors against P38A, CK2, MEK1 (to inhibit ERK signaling), PAK and PKC412 (which inhibits several kinases including the receptor tyrosine kinase Flt3, whose gene is often altered in AML). We chose to test these compounds because, while the involvement of CDKs in AML is well documented, the contribution of ERK1, PAK and CKs to AML biology is less well understood. PKC/Flt3i and P38αi served as negative controls as the K-scores of their kinase targets were found to be low in most cases. We obtained dose-response curves in 36 primary AML samples (FIG. 8), and $IC_{50}$ and SC values were computed (FIG. 7c). On average, primary AML cells were more sensitive to CK2i, PAK1i and MEK1i than to PKC/Flt3i and P38αi (FIG. 7c), consistent with the high K-scores for CK2A1, PAK1 and ERK1 relative to those for PKC/Flt3i and P38αi targets (PKCs/tyrosine kinases and P38A, respectively).

As with the cell-line data (FIG. 5), the predicted kinase activities reflected the sensitivity of cells to the inhibitors in primary AML blasts. Examples of data for two patient samples are shown in FIG. 7d and the data for the other patients are shown in FIG. 10. Linear regression analysis models showed that in 31 out of 36 biopsies K-scores and SCs were correlated with r>0.6 (FIG. 7e) and with an overall mean r=0.84. Interestingly, the MEK1 K-score was associated with the responses to the MEK1 inhibitor (FIG. 7f), irrespective of the mutation status of NRas or Kras (these having been previously linked to responses to MEK inhibitors in AML). Similarly, the JAK2 K-score (note that JAK2 acts downstream of Flt3) was weakly associated with sensitivity to PKC412 (which inhibits Flt3) across samples, and that this was a better predictor of sensitivity than Flt3 mutation status (FIG. 7g). Overall, these data indicate that models that use K-scores to quantify the contribution of kinases to the signaling output are able to predict the impact of inhibiting a given kinase on cell viability in cell-lines (FIG. 5) and primary cells (FIG. 7 d,e and FIG. 10).

Differences in Kinase Activities are Associated with the Complexity of Drug Response Phenotypes Instead of being resistant or sensitive to single compounds, the primary AML cells showed complex patterns of responses (FIG. 9a). For example, imposing a threshold of a 50% reduction in viability at 1 μM treatment, 10/36 cases were sensitive to at least three inhibitors (groups 1 to 5 in FIG. 9a), whereas 13/36 cases were resistant to all of the compounds (group 13). Five and three cases were sensitive to CKi only (group 11) or to MEK1i only (group 12), respectively. These phenotypes could not be rationalized by considering only the contribution of the target kinase. Therefore, we investigated patterns of kinase activities that may explain the observed heterogeneity in responses. While cytogenetic or FAB (French-American-British) classifications were not different across the response groups, there were marked differences in K-scores (FIG. 11a). For example, tyrosine kinases and PLK1 were increased in sensitive cells (groups 1-5) relative to resistant cells (group 13) and there was an inverse correlation between activities in cells sensitive to MEK1i only or to CK2i only (FIG. 11b-e). In MEK1i-sensitive cells (group 12), RAF K-scores were increased, whereas those for ATR were decreased relative to patient samples with other patterns of inhibition (FIG. 9b,c). Thus, the ratios of RAF to ATR K-scores were significantly greater in this group than in any other response group (FIG. 9d). Similarly, while the CK2A1 K-score was unexpectedly not greater in group 11 (cells sensitive to CK2i only, FIG. 9e), the PKCA K-score was significantly decreased in this group of samples (FIG. 9f) and the CK2A1: PKCA ratio was greater in CK2i sensitive cells relative to the other groups (FIG. 9g). Thus, in addition to activation of the target kinase, exclusive response to a given compound required an absence of activation of pro-survival pathways acting in parallel to the target.

The invention claimed is:

1. A method of treating a patient in need thereof with an inhibitor of a protein-modifying enzyme, comprising:
   (i) identifying and/or quantifying modified peptides in a sample from the patient using mass spectrometry (MS) comprising:
      (a) adding reference modified peptides to peptides obtained from the sample to produce a mixture of peptides and reference modified peptides;
      (b) carrying out mass spectrometry on the mixture to obtain data relating to the peptides from the sample; and
      (c) comparing the data relating to the peptides from the sample with data in a database of modified peptides to identify modified peptides in the sample;
   (ii) calculating a value K for each protein-modifying enzyme in the sample taken from said patient according to $$K = \frac{\sum_{i=1}^{m} \alpha_i}{\sum_{j=1}^{l} \beta_j},$$

wherein:
   m=the number of modified peptides in the sample that are substrates of the protein-modifying enzyme;
   α=the intensity of the modified peptides i;
   i=each modified peptide in the sample that is a substrate of the protein-modifying enzyme;
   l=the total number of modified peptides in the sample;
   β=the intensity of the modified peptides j; and
   j=all of the modified peptides in the sample;
   (iii) identifying the protein-modifying enzyme with the highest value K, wherein the protein-modifying enzyme is selected from: protein kinase A, protein kinase B, protein kinase C, protein kinase G, tyrosine kinase, tyrosine kinase-like kinase, calcium-dependent protein kinase, calmodulin-dependent protein kinase, the casein kinase 1 group; CMGC group, the homologues of yeast Sterile 7, Sterile 11, and Sterile 20 kinases;
   (iv) selecting an inhibitor that targets the protein-modifying enzyme with the highest value K; and
   (v) administering said inhibitor to said patient at a therapeutically effective amount, so as to treat the patient in a personalized manner.

2. The method according to claim 1, wherein the value K is modified by a correction factor and is calculated for said protein-modifying enzyme as follows:

$$K = \frac{\sum_{i=1}^{m} \alpha_i}{\sum_{j=1}^{l} \beta_j} * \left(\frac{m}{t}\right)^{1/2}$$

wherein t=the total number of known target modified peptides for said protein-modifying enzyme.

3. The method according to claim 1, wherein the inhibitor is AZD-5438, GF-109203X, PF-3758309, GSK1120212, MK-2206, KU-0063794, TAK 715, PKC-412, TBB, or C4945.

4. The method according to claim 1, wherein the database of modified peptides is compiled by a method comprising:
   i) obtaining peptides from a sample;
   ii) enriching modified peptides from the peptides obtained in step i);
   iii) carrying out liquid chromatography-tandem mass spectrometry (LC-MS/MS) on the enriched modified peptides obtained in step ii);
   iv) comparing the modified peptides detected in step iii) to a known reference database in order to identify the modified peptides; and
   v) compiling data relating to the modified peptides identified in step iv into a database.

5. The method according to claim 4, wherein the data relating to the peptides in the sample comprises the mass to charge (m/z) ratio, charge (z), and relative retention time of the peptides.

6. The method according to claim 4, wherein step ii) is carried out using multidimensional chromatography.

7. The method according to claim 6, wherein the multidimensional chromatography is carried out using strong cation exchange high performance liquid chromatography (SCX-HPLC), immobilized metal ion affinity chromatography (IMAC), and titanium dioxide (TiO2) chromatography.

8. The method according to claim 6, wherein the multidimensional chromatography is carried out using anion exchange high performance liquid chromatography (SAX-HPLC), immobilized metal ion affinity chromatography (IMAC), and titanium dioxide (TiO2) chromatography.

9. The method according to claim 4, wherein step ii) is carried out using antibody-based methods.

10. The method according to claim 4, wherein step iv) is carried out using a search engine that uses mass spectrometry data to identify proteins in one or more primary sequence databases, including the known reference database.

11. The method according to claim 4, wherein the data relating to the modified peptides identified in step iv) is selected from the group consisting of identity of the modified peptide, mass to charge (m/z) ratio, charge (z), and relative retention time of the modified peptide.

12. The method according to claim 1, wherein step b) further comprises enriching modified peptides from said mixture of peptides and reference modified peptides to produce a mixture of enriched modified peptides, and step c) comprises carrying out mass spectrometry (MS) on said mixture of enriched modified peptides to obtain data relating to the modified peptides in the sample.

13. The method according to claim 12, wherein the step of enriching modified peptides is carried out using chromatography.

14. The method according to claim 13, wherein the chromatography is selected from the group consisting of immobilized metal ion affinity chromatography (IMAC), titanium dioxide ($TiO_2$) chromatography, and zirconium dioxide ($ZrO_2$) chromatography.

15. The method according to claim 12, wherein the step of enriching modified peptides is carried out using antibody-based methods.

16. The method according to claim 12, wherein said mass spectrometry (MS) in step c) is liquid chromatography-mass spectrometry (LC-MS).

17. The method according to claim 1, wherein the MS technique uses isotope labels for quantification.

* * * * *